US010053443B2

(12) United States Patent
Lee et al.

(10) Patent No.: US 10,053,443 B2
(45) Date of Patent: Aug. 21, 2018

(54) 2-PHENYLBENZOFURAN DERIVATIVES, METHOD FOR PREPARING THE SAME AND USE OF THE SAME FOR TREATING INFLAMMATORY DISEASE

(71) Applicants: KOREA RESEARCH INSTITUTE OF BIOSCIENCE AND BIOTECHNOLOGY, Daejeon (KR); DONGGUK UNIVERSITY INDUSTRY-ACADEMIC COOPERATION FOUNDATION, Seoul (KR)

(72) Inventors: Kyeong Lee, Seoul (KR); Sei-Ryang Oh, Daejeon (KR); Kyung Seop Ahn, Daejeon (KR); Ok-Kyoung Kwon, Daejeon (KR); Doo-Young Kim, Daejeon (KR); Hyung Won Ryu, Daejeon (KR); Jung Hee Kim, Daejeon (KR); Xuezhen Xu, Goyang-si (KR)

(73) Assignees: KOREA RESEARCH INSTITUTE OF BIOSCIENCE AND BIOTECHNOLOGY, Daejeon (KR); DONGGUK UNIVERSITY INDUSTRY—ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/449,465

(22) Filed: Mar. 3, 2017

(65) Prior Publication Data
US 2017/0174645 A1    Jun. 22, 2017

Related U.S. Application Data

(63) Continuation-in-part of application No. 15/221,025, filed on Jul. 27, 2016, which is a continuation of application No. PCT/KR2015/000922, filed on Jan. 28, 2015.

(30) Foreign Application Priority Data

Jan. 28, 2014    (KR) ........................ 10-2014-0010224
Jan. 28, 2015    (KR) ........................ 10-2015-0013199

(51) Int. Cl.
*A61K 31/343*    (2006.01)
*C07D 307/86*    (2006.01)
*A23L 33/10*    (2016.01)

(52) U.S. Cl.
CPC ............ *C07D 307/86* (2013.01); *A23L 33/10* (2016.08); *A61K 31/343* (2013.01); *A23V 2002/00* (2013.01)

(58) Field of Classification Search
CPC ... C07D 307/86; A23L 33/10; A23V 2002/00; A61K 31/343
See application file for complete search history.

(56) References Cited

FOREIGN PATENT DOCUMENTS

| JP | 11-158067 A | 6/1999 |
|----|-------------|--------|
| WO | 2006023778 A2 | 3/2006 |
| WO | 2010/037210 A1 | 4/2010 |

OTHER PUBLICATIONS

Schreiber et al (Chemistry Letters, 1975, 12, 1257-8).*
Scammels et al (Bioorganic & Medicinal Chemistry, 1998, 6(9), 1517-1524).*
Lee et al (Bulletin of the Korean Chemical Society (2012), 33(6), 1907-1912).*
H.Y. Sung, et al; Novel danshen methoxybenzo[b]furan derivative . . . ; Chemico-Biological Interactions; vol. 188; 2010; pp. 457-466.
M. Perreault, et al; Targeted disruption of inducible nitric oxide synthase protects . . . ; Nature Medicine; vol. 7; No. 10; 2001; pp. 1138-1143.
C.L. Kao, et al; A convenient synthesis of naturally occurring benzofuran ailanthoidol; Tetrahedron Letters; vol. 42; 2001; pp. 1111-1113.
J.W. Hwang, et al; Facile preparation of 2-arylbenzo[b]furan molecules and their . . . ; Bull. Korean Chem. Soc.; vol. 31; No. 4; 2010; pp. 965-970.
Facile Preparation of 2-Arylbenzolblfuran Molecules and Their Anti-inflammatory Effects, Bull. Korean Chem. Soc. 2010, vol. 31, No. 4 965.
Structural Characterization of Guaiacyl-rich Lignins in Flax (Linum usitatissimum) Fibers and Shives , J. Med. Chem. 2008, 51, 842-851.
Alternate and Efficient Method for the Total Synthesis of Egonol via Sonogashira Coupling Reaction, M. Naveen, et al, J. Heterocyclic Chem., 50, 1064(2013).
Recherches sur le benzofuranne, LVII. Sur une chloration inhabituelle de l'heterocycle au cours de la reduction des (nitro-4 phenyl)-2 ou -3 benzo-furannes par le chlorure stanneux, J. Heterocyclic Chem., 14, 803(1977).

* cited by examiner

*Primary Examiner* — Sudhakar Katakam
(74) *Attorney, Agent, or Firm* — Lucas & Mercanti, LLP

(57) ABSTRACT

The present invention relates to a novel 2-phenylbenzofuran derivative or a pharmaceutically acceptable salt thereof, a production method for the same, and a pharmaceutical composition for preventing or treating an inflammatory disease comprising the same as an active ingredient, and the novel 2-phenylbenzofuran derivative or the pharmaceutically acceptable salt thereof according to the present invention is outstandingly effective in suppressing NO, IL-6, and TNF-alpha induced by macrophages, and therefore can advantageously be used in a pharmaceutical composition for preventing or treating an inflammatory disease.

10 Claims, 8 Drawing Sheets

2-PHENYLBENZOFURAN DERIVATIVES, METHOD FOR PREPARING THE SAME AND USE OF THE SAME FOR TREATING INFLAMMATORY DISEASE

CROSS-REFERENCE TO RELATED APPLICATIONS

This application is a continuation-in-part of U.S. patent application Ser. No. 15/221 025 filed Jul. 27, 2016, which is a continuation of PCT/KR2015/000922, filed Jan. 28, 2015, which claims the benefit of Korean Patent Application Nos. 10-2014-0010224 filed Jan. 28, 2014 and 10-2015-0013199 filed Jan. 28, 2015, the contents of each of which are incorporated herein by reference.

BACKGROUND OF THE INVENTION

Field of the Invention

The present invention relates to a novel 2-phenylbenzofuran derivative or a pharmaceutically acceptable salt thereof, a production method for the same, and a pharmaceutical composition for preventing or treating an inflammatory disease comprising the same as an active ingredient Description of the Related Art Inflammation is a kind of defense reaction in a living body against a foreign infectious agent including a physical •chemical stimulus, bacteria, fungi, virus, and various allergens. Inflammatory response is a part of innate immune response. Like in animals, the innate immune response in human starts with the macrophage's attack to a pathogen when the macrophage recognizes the pathogen as a non-self by catching a specific pattern on the cell surface of the pathogen. In the course of inflammatory response, blood plasma is accumulated in the area of inflammation to dilute the toxicity caused by bacteria, and also blood flow increases and such symptoms as erythema, pain, edema, and fever accompany.

Various biochemical phenomena are involved in the inflammatory response. In particular, it is known that nitric oxide synthase (NOS) and cyclooxygenase (COX) involved in the biosynthesis of various prostaglandins are important mediators of inflammatory response.

NOS has three isomers, which are calcium or camodulin dependent eNOS (endothelial NOS) and nNOS (neuronal NOS), and iNOS (inducible NOS) induced by bacterial endotoxin such as LPS (lipopolysaccharide) and various inflammatory cytokines such as IL-1β, TNF-α, IL-6, IL-8, and IL-12. They produce nitric oxide (NO) from L-arginine.

Nitric oxide (NO) generated by eNOS or nNOS is involved in various physiological responses including blood pressure regulation, neurotransmission, learning, and memory, indicating that NO plays an important role in maintaining homeostasis in a human body. In the meantime, NO generated by iNOS is involved in various inflammatory diseases such as arthritis, sepsis, graft rejection, autoimmune disease, and neuronal death (non-patent references 1 and 2).

LPS, one of those components forming a cell wall of gram-negative bacteria, is able to activate macrophages, due to which it is often used for an inflammatory model. Once macrophages are activated by LPS, inflammation precursors such as cytokines, chemokines, and NO are secreted, which sometimes even show a cancerous activity. The over-expressions of those inflammation mediators such as cytokines, chemokines, and NO are observed in various diseases including sepsis, rheumatoid arthritis, autoimmune disease, and diabetes. So, a substance that can regulate the inflammatory response by controlling macrophages can be an important target for the treatment of inflammatory disease.

Therefore, a substance that can suppress the over-expressions of such inflammation mediators as described above can be developed as a therapeutic agent for the treatment of inflammatory disease.

Thus, the present inventors tried to develop a compound that could suppress nitric oxide (NO), IL-6, and TNF-alpha in macrophages. In the course of our study, the present inventors confirmed that a 2-phenylbenzofuran derivative with a specific structure was excellent in suppressing NO, IL-6, and TNF alpha, and thereby confirmed that the 2-phenylbenzofuran derivative can be effectively used as a composition for preventing and treating inflammatory disease, leading to the completion of this invention.

REFERENCE

Moncade S. et al, Pharmacol. Rev., 1991, 43, 109;
Perreault M. and Marette A. Nature Medicine, 2001, 7, 1138.

SUMMARY OF THE INVENTION

It is an object of the present invention to provide a novel 2-phenylbenzofuran derivative or a pharmaceutically acceptable salt of the same.

It is another object of the present invention to provide a method for preparing the 2-phenylbenzofuran derivative above.

It is also an object of the present invention to provide a pharmaceutical composition comprising the novel 2-phenylbenzofuran derivative or the pharmaceutically acceptable salt thereof as an active ingredient for preventing or treating inflammatory disease.

It is further an object of the present invention to provide a health food composition comprising the novel 2-phenylbenzofuran derivative or the pharmaceutically acceptable salt thereof as an active ingredient for preventing or improving inflammatory disease.

To achieve the above objects, the present invention provides a 2-phenylbenzofuran derivative represented by formula 1 or formula 2 or a pharmaceutically acceptable salt thereof:

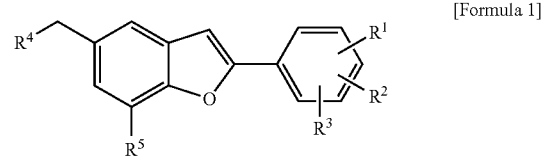

[Formula 1]

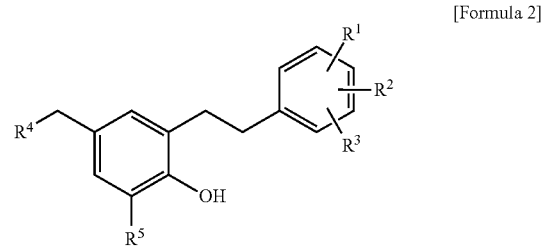

[Formula 2]

In the formula 1 and formula 2, $R^1$, $R^2$ and $R^3$ are independently selected from the group consisting of hydrogen, hydroxy, halogen, straight or branched $C_{1-6}$ alkyl which is unsubstituted or substituted with one or more halogen, straight or branched $C_{1-6}$ alkoxy, and amino which is substituted with one or more straight or branched $C_{1-6}$ alkyl;

$R^4$ is hydroxy, $C_{1-6}$ hydroxyalkyl, or $R^6(C=O)O(CH_2)n-$, wherein $R^6$ is straight or branched $C_{1-3}$ alkyl, and n is an integer of 1~6; and $R^5$ is hydroxy, or straight or branched $C_{1-6}$ alkoxy.

The present invention also provides a method for preparing the 2-phenylbenzofuran derivative above.

In addition, the present invention provides a pharmaceutical composition comprising the novel 2-phenylbenzofuran derivative or the pharmaceutically acceptable salt thereof as an active ingredient for preventing or treating inflammatory disease.

Further, the present invention provides a health food composition comprising the novel 2-phenylbenzofuran derivative or the pharmaceutically acceptable salt thereof as an active ingredient for preventing or improving inflammatory disease.

The novel 2-phenylbenzofuran derivative or the pharmaceutically acceptable salt thereof of the present invention is excellent in suppressing NO, IL-6, and TNF-alpha induced by macrophages, so that it can be effectively used for a pharmaceutical composition for preventing or treating inflammatory disease.

DETAILED DESCRIPTION OF THE INVENTION

Figure 1:
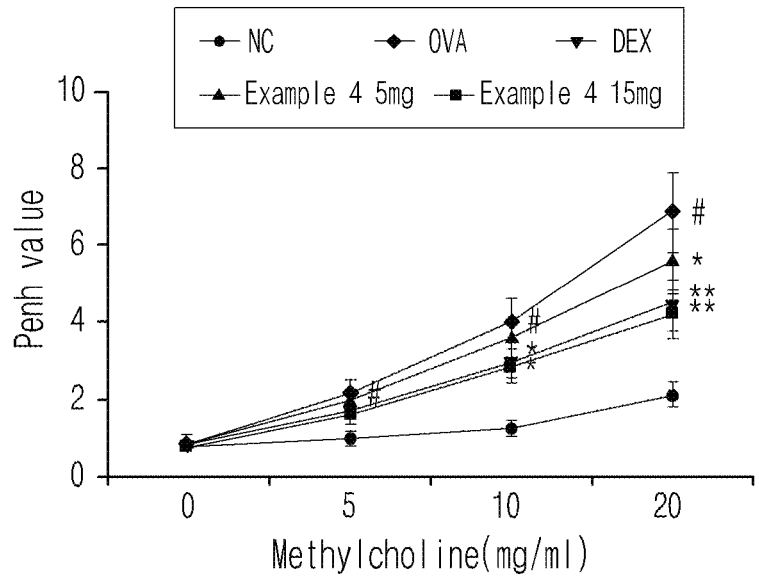
FIG. 1 is a graph illustrating the changes of airway hyperreactivity resulted from asthma development, investigated in Experimental Example <3-2> of the present invention.

Hereinafter, the present invention is described in detail.

The present invention provides a 2-phenylbenzofuran derivative represented by formula 1 or formula 2 or a pharmaceutically acceptable salt thereof:

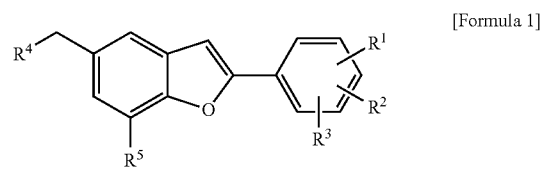

[Formula 1]

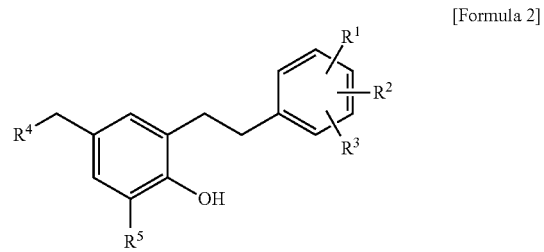

[Formula 2]

In the formula 1 and formula 2, $R^1$, $R^2$ and $R^3$ are independently selected from the group consisting of hydrogen, hydroxy, halogen, straight or branched $C_{1-6}$ alkyl which is unsubstituted or substituted with one or more halogen, straight or branched $C_{1-6}$ alkoxy, and amino which is substituted with one or more straight or branched $C_{1-6}$ alkyl;

$R^4$ is hydroxy, $C_{1-6}$ hydroxyalkyl, or $R^6(C=O)O(CH_2)n-$, wherein $R^6$ is straight or branched $C_{1-3}$ alkyl, and n is an integer of 1~6; and $R^5$ is hydroxy, or straight or branched $C_{1-6}$ alkoxy.

Preferably, $R^1$, $R^2$, and $R^3$ are independently selected from the group consisting of hydrogen, hydroxy, chlorine, fluorine, straight or branched $C_{1-4}$ alkyl which is unsubstituted or substituted with one or more halogen, straight or branched $C_{1-4}$ alkoxy, and amino which is substituted with one or more straight or branched $C_{1-4}$ alkyl. More preferably, $R^1$, $R^2$, and $R^3$ are independently selected from the group consisting of hydrogen, hydroxy, chlorine, fluorine, trifluoromethyl, methoxy, ethoxy, dimethylamino, and diethylamino.

$R^4$ is preferably selected from the group consisting of hydroxymethyl, hydroxyethyl, hydroxypropyl, and $CH_3(C=O)O(CH_2)_3-$.

$R^5$ is preferably selected from the group consisting of hydroxy, methoxy, and ethoxy.

The 2-phenylbenzofuran derivative represented by formula 1 or formula 2 is exemplified more precisely by the followings:

1) 3-[2-(3,4-dimethoxyphenyl)-7-methoxybenzofuran-5-yl]propane-1-ol;
2) 3-(7-methoxy-2-(4-methoxy-2-methylphenyl)benzofuran-5-yl)propane-1-ol;
3) 3-(7-methoxy-2-m-tolylbenzofuran-5-yl)propane-1-ol;
4) 3-(7-methoxy-2-p-tolylbenzofuran-5-yl)propane-1-ol;
5) 3-(7-methoxy-2-(3-methoxyphenyl)benzofuran-5-yl)propane-1-ol;
6) 3-[2-(3,5-difluorophenyl)-7-methoxybenzofuran-5-yl]propane-1-ol;
7) 3-(7-methoxy-2-(4-methoxyphenyl)benzofuran-5-yl)propane-1-ol;
8) 3-(2-(3-fluorophenyl)-7-methoxybenzofuran-5-yl)propane-1-ol;
9) 3-(2-(4-(dimethylamino)phenyl)-7-methoxybenzofuran-5-yl)propane-1-ol;
10) 3-(7-methoxy-2-(2-methoxyphenyl)benzofuran-5-yl)propane-1-ol;
11) 3-(7-methoxy-2-(3-(trifluoromethyl)phenyl)benzofuran-5-yl)propane-1-ol;
12) 3-[2-(3,5-dimethoxyphenyl)-7-methoxybenzofuran-5-yl]propane-1-ol;
13) 3-(7-methoxy-2-(4-(trifluoromethyl)phenyl)benzofuran-5-yl) propane-1-ol;
14) 2-(3,4-dimethoxyphenethyl)-4-(3-hydroxypropyl)-6-methoxyphenol;
15) 4-(3-hydroxypropyl)-2-methoxy-6-(3-methylpenethyl)phenol;
16) 4-(3-hydroxypropyl)-2-methoxy-6-(4-methylpenethyl)phenol;
17) 4-(3-hydroxypropyl)-2-methoxy-6-(3-methoxypenethyl)phenol;
18) [2-(3,4-dimethoxyphenyl)-7-methoxybenzofuran-5-yl]methanol;
19) (7-methoxy-2-(4-methoxy-2-methylphenyl)benzofuran-5-yl)methanol;
20) 2-[2-(3,4-dimethoxyphenyl)-7-methoxybenzofuran-5-yl]ethanol;
21) 2-(7-methoxy-2-(4-methoxy-2-methylphenyl)benzofuran-5-yl)ethanol;
22) 4-(5-(3-hydroxypropyl)-7-methoxybenzofuran-2-yl)-2-methoxyphenol;
23) 5-(5-(3-hydroxypropyl)-7-methoxybenzofuran-2-yl)-2-methoxyphenol;
24) 5-(5-(3-hydroxypropyl)-7-methoxybenzofuran-2-yl)benzene-1,3-diol;
25) 4-(5-(3-hydroxypropyl)-7-methoxybenzofuran-2-yl)benzene-1,2-diol;
26) 4-(5-(3-hydroxypropyl)-7-methoxybenzofuran-2-yl)-2,6-dimethoxyphenol;
27) 2-(3,4-dimethoxyphenyl)-5-(3-hydroxypropyl)benzofuran-7-ol; and
28) 3-(2-(3,4-dimethoxyphenyl)-7-methoxybenzofuran-5-yl)propyl acetate.

The 2-phenylbenzofuran derivative represented by formula 1 or formula 2 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the 2-phenylbenzofuran derivative represented by formula 1 or formula 2 is dissolved in an organic solvent such as methanol, ethanol, acetone, methylenechloride, or acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the 2-phenylbenzofuran derivative represented by formula 1 or formula 2 but also a pharmaceutically acceptable salt thereof, and a solvate, an optical isomer, or a hydrate possibly produced from the same.

The present invention also provides a method for preparing the 2-phenylbenzofuran derivative represented by formula 1 or formula 2.

Preparation Method 1:

The present invention provides a method for preparing the derivative represented by formula 1 of claim 1 comprising the following steps, as shown in reaction formula 1 below:

preparing the compound represented by formula 5 via Sonogashira reaction by reacting the compound represented by formula 3 with the compound represented by formula 4 in the presence of a palladium/charcoal catalyst and a base (step 1); and preparing the compound represented by formula 1a by reducing the compound represented by formula 5 obtained in step 1 in the presence of sodiumborohydride (step 2):

[Reaction Formula 1]

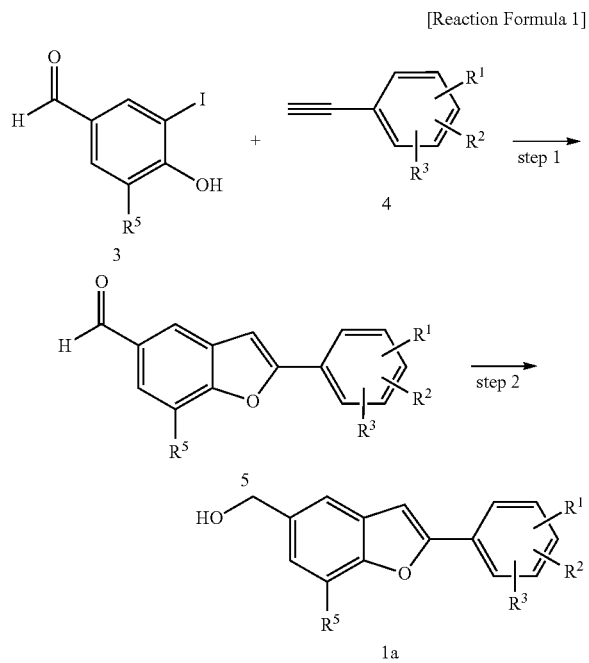

In the reaction formula 1, $R^1$, $R^2$, $R^3$, and $R^5$ are as defined in claim 1, and the compound represented by formula 1a is a derivative of the compound represented by formula 1 of claim 1.

Hereinafter, the preparation method 1 is described in more detail step by step.

In the preparation method 1 of the present invention, step 1 is to give the compound represented by formula 5 by inducing Sonogashira reaction and cyclization of the compound represented by formula 3 and the compound represented by formula 4 in the presence of a palladium/charcoal catalyst and a base.

Particularly, the said Sonogashira reaction is the reaction to produce carbon-carbon bond by substituting halogen with alkyne by using a palladium catalyst via organic synthesis. And, the said cyclization is the reaction to produce a ring by adding a hydroxy group of the compound represented by formula 3 to the Alkyne substituted by Sonogashira reaction.

At this time, the palladium catalyst used for the Sonogashira reaction in step 1 is not limited and any conventional palladium catalyst acceptable for Sonogashira reaction can be used but preferably selected from the group consisting of palladium charcoal (Pd/C), tetrakistriphenylphosphinepalladium ($Pd(PPh_3)_4$), bistriphenylpalladiumdichloride ($PdCl_2(PPh_3)_2$), trisdibenzylideneacetonepalladium ($Pd_2(dba)_3$), 1,1-bis(diphenylphosphinoferrocene)dichloropalladium ($PdCl_2(dppf)$), arylpalladiumchloridedimer ($[PdCl(allyl)]_2$), diacetatepalladium ($Pd(OAc)_2$), and palladiumdichloride ($PdCl_2$), and more preferably palladium charcoal (Pd/C) is selected.

The base in step 1 is exemplified by such an organic acid as triethylamine, N,N-diisopropylethylamine, 1,8-diazabicyclo[5.4.0]-7-undecene (DBU), pyridine, and L-prolinol or such an inorganic base as sodium carbonate, potassium carbonate, potassium hydroxide, sodium hydroxide, cesium carbonate, and barium hydroxide, which is used by equivalent or excessive amount.

Further, the solvent used in step 1 is preferably selected form the group consisting of water, tetrahydrofuran, dioxane, 1,2-dimethoxyethane, benzene, toluene, xylene, methanol, ethanol, propanol, butanol, dimethylformamide (DMF), dimethylsulfoxide (DMSO), and acetonitrile, which is used independently or together. Among these, water is more preferred.

Also, the reaction of step 1 is preferably induced at 0° C. or under the boiling point of a solvent.

In the preparation method 1 of the present invention, step 2 is to give the compound represented by formula 1a by inducing reduction of the compound represented by formula 5 obtained in step 1.

Particularly in step 2, an aldehyde group of the compound represented by formula 5 is converted into an alcohol group.

At this time, a reagent for the reduction above is not limited and any conventional reagent that is able to reduce aldehyde is accepted without limitation, but is preferably selected from the group consisting of sodiumborohydride ($NaBH_4$) and lithiumaluminumhydride ($LiAlH_4$), and sodiumborohydride ($NaBH_4$) is more preferred.

The solvent used in step 2 is preferably selected from the group consisting of tetrahydrofuran, dioxane, 1,2-dimethoxyethane, benzene, toluene, xylene, methanol, ethanol, propanol, butanol, dimethylformamide (DMF), dimethylsulfoxide (DMSO), and acetonitrile, which is used independently or together. Among these, tetrahydrofuran is more preferred.

Also, the reaction of step 2 is preferably induced at 0° C. or under the boiling point of a solvent.

Preparation Method 2:

The present invention also provides a method for preparing the derivative represented by formula 1 of claim 1 comprising the following steps, as shown in reaction formula 2:

preparing the compound represented by formula 6 by reacting the compound represented by formula 5 with methyltriphenylphosphine halide and removing water from the same in the presence a base catalyst (step 1); and preparing the compound represented by formula 1b by inducing hydroboration using borane or diborane and oxidation using hydrogen peroxide of the compound represented by formula 6 obtained in step 1 (step 2):

[Reaction Formula 2]

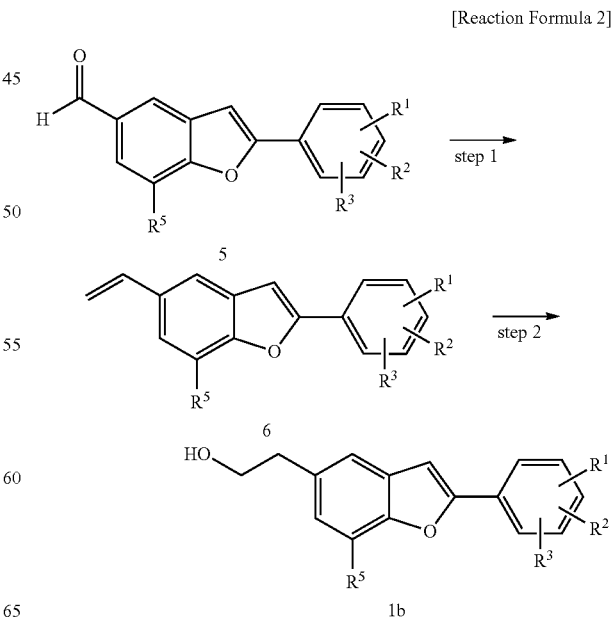

In the reaction formula 2, $R^1$, $R^2$, $R^3$, and $R^5$ are as defined in claim 1, and the compound represented by formula 1b is a derivative of the compound represented by formula 1 of claim 1.

Hereinafter, the preparation method 2 is described in more detail step by step.

In the preparation method 2 of the present invention, step 1 is to give the compound represented by formula 6 by reacting the compound represented by formula 5 with methyltriphenylphosphine halide and removing water from the same in the presence a base catalyst.

Particularly, an aldehyde group of the compound represented by formula 5 is reacted with methyltriphenylphosphine halide and then water is removed in the presence of a base catalyst, resulting in the compound represented by formula 6 containing a vinyl group.

At this time, the methyltriphenylphosphine halide is preferably methyltriphenylphosphine iodide ($CH_3PPh_3I$).

The base in step 1 is preferably sodium hydride, potassium hydride, lithium hydride, or cesium hydride, and sodium hydride is more preferred.

The solvent in step 1 is preferably exemplified by dimethylformamide, dimethylsulfoxide, and acetonitrile.

Also, the reaction of step 2 is preferably induced at 0° C. or under the boiling point of a solvent.

In the preparation method 2 of the present invention, step 2 is to give the compound represented by formula 1b by inducing hydroboration and oxidation of the compound represented by formula 6 obtained in step 1.

Particularly, step 2 is to give the compound represented by formula 1b comprising a primary alcohol group by inducing hydroboration of an alkene group of the compound represented by formula 6, and oxidation of the same.

At this time, borane ($BH_3$) or diborane ($B_2H_6$) is preferably used for the hydroboration as a boron compound, and hydrogen peroxide ($H_2O_2$) is preferably used for the oxidation.

The base used in step 2 is an inorganic base selected from the group consisting of sodium hydroxide, potassium hydroxide, lithium hydroxide, barium hydroxide, sodium carbonate, potassium carbonate and cesium carbonate, which is used by equivalent or excessive amount.

Preparation Method 3:

The present invention also provides a method for preparing the derivative represented by formula 1 of claim 1 comprising the following steps, as shown in reaction formula 3 below:

preparing the compound represented by formula 8 by reacting the compound represented by formula 5 with the compound represented by formula 7 in the presence of a base catalyst (step 1);

preparing the compound represented by formula 9 by inducing hydrogenation of the compound represented by formula 8 obtained in step 1 in the presence of an acid using palladium charcoal as a catalyst (step 2); and preparing the compound represented by formula 1c by reducing the compound represented by formula 9 obtained in step 2 in the presence of sodium borohydride (step 3):

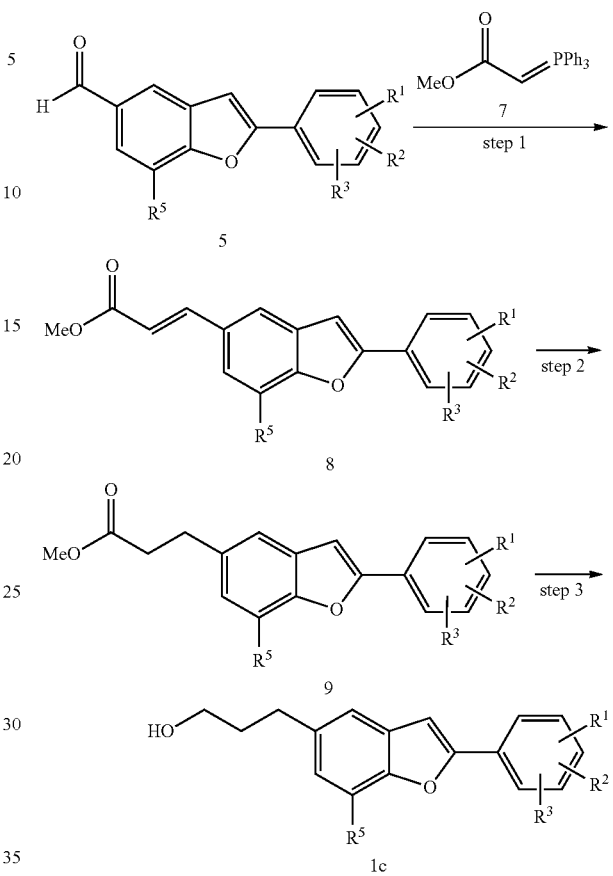

[Reaction Formula 3]

In the reaction formula 3, $R^1$, $R^2$, $R^3$, and $R^5$ are as defined in claim 1, and the compound represented by formula 1c is a derivative of the compound represented by formula 1 of claim 1.

Hereinafter, the preparation method 3 is described in more detail step by step.

In the preparation method 3 of the present invention, step 1 is to give the compound represented by formula 8 by reacting the compound represented by formula 5 with the compound represented by formula 7.

Particularly, this step is performed by the same manner as step 1 of the preparation method 2 above except that the compound represented by formula 7 is used instead of methyltriphenylphosphine halide.

In the preparation method 3 of the present invention, step 2 is to give the compound represented by formula 9 by inducing hydrogenation of the compound represented by formula 8 obtained in step 1.

Particularly, an alkene group of the compound represented by formula 8 is hydrogenated to produce an alkyl group.

At this time, the hydrogenation is not limited and performed as generally. Preferably, the reaction is performed in the presence of an acid using palladium charcoal as a catalyst.

The solvent used in step 2 is preferably selected from the group consisting of tetrahydrofuran, 1,2-dimethoxyethane, benzene, toluene, xylene, dimethylformamide, dimethylsulfoxide, and acetonitrile, which is used independently or together. Among these, tetrahydrofuran is more preferred.

Also, the reaction of step 2 is preferably induced at 0° C. or under the boiling point of a solvent.

In the preparation method 3 of the present invention, step 3 is to give the compound represented by formula 1c by reducing the compound represented by formula 9 obtained in step 2.

Particularly, this step is performed by the same manner as step 2 of the preparation method 1.

Preparation Method 4:

The present invention also provides a method for preparing the derivative of formula 2 of claim 1 comprising the following steps, as shown in reaction formula 4:

preparing the compound represented by formula 10 by inducing hydrogenation of the compound represented by formula 7 in the presence of an acid using palladium charcoal as a catalyst (step 1); and preparing the compound represented by formula 2a by reducing the compound represented by formula 10 obtained in step 1 in the presence of sodium borohydride (step 2):

[Reaction Formula 4]

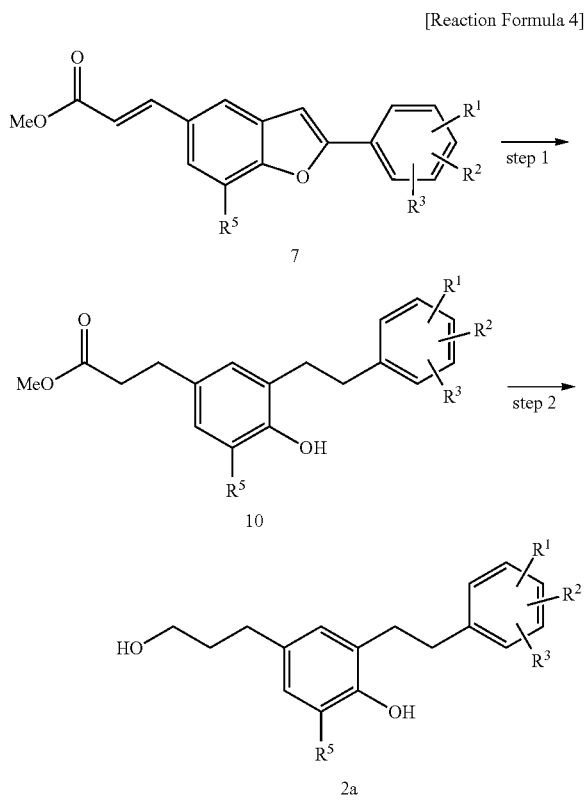

In the reaction formula 4, $R^1$, $R^2$, $R^3$, and $R^5$ are as defined in claim 1, and the compound represented by formula 2a is a derivative of the compound represented by formula 2 of claim 1.

Hereinafter, the preparation method 4 is described in more detail step by step.

In the preparation method 4 of the present invention, step 1 is to give the compound represented by formula 10 by inducing hydrogenation of the compound represented by formula 7.

Particularly, step 1 is to give the compound represented by formula 10 by inducing hydrogenation of the compound represented by formula 7, wherein an alkene group is converted into an alkyl group and the furan ring of the benzofuran group becomes open.

At this time, the hydrogenation is induced by the same manner as or similarly to step 2 of the preparation method 3 above.

In the preparation method 4 of the present invention, step 2 is to give the compound represented by formula 2a by reducing the compound represented by formula 10 obtained in step 1.

Particularly, this step is performed by the same manner as step 2 of the preparation method 1.

In those preparation methods 1~4, after the reaction of each step, additional steps of extracting with an organic solvent, drying, filtering, and distillating under reduced pressure can be performed and also column chromatography or re-crystallization can be performed.

The present invention also provides a pharmaceutical composition comprising the novel 2-phenylbenzofuran derivative or the pharmaceutically acceptable salt thereof as an active ingredient for preventing or treating inflammatory disease.

The inflammatory disease herein is preferably selected from the group consisting of dermatitis, allergy, atopy, conjunctivitis, periodontitis, rhinitis, otitis media, laryngopharyngitis, tonsilitis, pneumonia, gastric ulcer, gastritis, Crohn's disease, colitis, hemorrhoid, gout, ankylosing spondylitis, rheumatic fever, lupus, fibromyalgia, psoriatic arthritis, osteoarthritis, rheumatoid arthritis, periarthritis of shoulder, tendinitis, tenosynovitis, peritendinitis, dermatitis, hepatitis, cystitis, nephritis, Sjogren's syndrome, multiple sclerosis, asthma, COPD (Chronic Obstructive Pulmonary Disease) and acute or chronic inflammatory disease.

Particularly, the 2-phenylbenzofuran derivative of the present invention displays an excellent cell survival rate with low cytotoxicity (experimental example 1), as high NO generation suppression rate as at least 30% by immune response (experimental example 2-1). The 2-phenylbenzofuran derivative of the invention is also excellent in suppressing the generation of IL-6 generation by immune response (experimental example 2-2) and is excellent in suppressing the generation of TNF-alpha by immune response as well (experimental example 2-3).

Therefore, the 2-phenylbenzofuran derivative represented by formula 1 or formula 2 of the present invention or the pharmaceutically acceptable salt thereof can be used as an active ingredient for a pharmaceutical composition for preventing or treating inflammatory disease.

The 2-phenylbenzofuran derivative represented by formula 1 or formula 2 of the present invention or the pharmaceutically acceptable salt thereof can be prepared for oral or parenteral administration by mixing with generally used diluents or excipients such as fillers, extenders, binders, wetting agents, disintegrating agents and surfactants.

The formulations for oral administration are exemplified by tablets, pills, powders, granules, capsules, and troches, etc. The solid formulations for oral administration are prepared by mixing one or more suitable excipients such as starch, calcium carbonate, sucrose or lactose, gelatin, etc. in addition to the 2-phenylbenzofuran derivative represented by formula 1 or formula 2 of the present invention or the pharmaceutically acceptable salt thereof. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations, and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The effective dosage of the 2-phenylbenzofuran derivative represented by formula 1 or formula 2 of the present invention or the pharmaceutically acceptable salt thereof can be determined according to age, weight, gender, administration method, health condition, and severity of disease. The dosage is 0.1~1000 mg/day for an adult patient (70 Kg), preferably 1~500 mg/day, which can be administered several times a day or preferably once a day or a couple of times a day.

The pharmaceutical composition of the present invention can be administered alone or treated together with surgical operation, hormone therapy, chemo-therapy and biological regulators.

The present invention also provides a health food composition comprising the novel 2-phenylbenzofuran derivative or the pharmaceutically acceptable salt thereof as an active ingredient for preventing or improving inflammatory disease.

The inflammatory disease herein is preferably selected from the group consisting of dermatitis, allergy, atopy, conjunctivitis, periodontitis, rhinitis, otitis media, laryngopharyngitis, tonsilitis, pneumonia, gastric ulcer, gastritis, Crohn's disease, colitis, hemorrhoid, gout, ankylosing spondylitis, rheumatic fever, lupus, fibromyalgia, psoriatic arthritis, osteoarthritis, rheumatoid arthritis, periarthritis of shoulder, tendinitis, tenosynovitis, peritendinitis, dermatitis, hepatitis, cystitis, nephritis, Sjogren's syndrome, multiple sclerosis, asthma, COPD(Chronic Obstructive Pulmonary Disease) and acute or chronic inflammatory disease.

Particularly, the 2-phenylbenzofuran derivative of the present invention displays an excellent cell survival rate with low cytotoxicity (experimental example 1), as high NO generation suppression rate as at least 30% by immune response (experimental example 2-1). The 2-phenylbenzofuran derivative of the invention is also excellent in suppressing the generation of IL-6 generation by immune response (experimental example 2-2) and is excellent in suppressing the generation of TNF-alpha by immune response as well (experimental example 2-3).

Therefore, the 2-phenylbenzofuran derivative represented by formula 1 or formula 2 of the present invention or the pharmaceutically acceptable salt thereof can be used as an active ingredient for a health food composition for preventing or improving inflammatory disease.

The food herein is not limited. For example, the derivative of the present invention can be added to drinks, meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The 2-phenylbenzofuran derivative represented by formula 1 or formula 2 of the present invention or the pharmaceutically acceptable salt thereof can be used as a food additive. In that case, the 2-phenylbenzofuran derivative represented by formula 1 or formula 2 of the present invention or the pharmaceutically acceptable salt thereof can be added as it is or as mixed with other food components according to the conventional method. The mixing ratio of active ingredients can be regulated according to the purpose of use (prevention or improvement). In general, to produce health food or beverages, the 2-phenylbenzofuran derivative represented by formula 1 or formula 2 of the present invention or the pharmaceutically acceptable salt thereof is added preferably by 0.1~90 weight part. However, if long term administration is required for health and hygiene or regulating health condition, the content can be lower than the above but higher content can be accepted as well since the 2-phenylbenzofuran derivative represented by formula 1 or formula 2 of the present invention or the pharmaceutically acceptable salt thereof has been proved to be very safe.

The health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 g of the composition of the present invention.

In addition to the ingredients mentioned above, the 2-phenylbenzofuran derivative represented by formula 1 or formula 2 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The 2-phenylbenzofuran derivative of the present invention can also include natural fruit juice, fruit beverages and/or fruit flesh addable to vegetable beverages.

Practical and presently preferred embodiments of the present invention are illustrative as shown in the following Examples.

However, it will be appreciated that those skilled in the art, on consideration of this disclosure, may make modifications and improvements within the spirit and scope of the present invention.

PREPARATIVE EXAMPLE 1

2-(3,4-dimethoxyphenyl)-7-methoxybenzofuran-5-carbaldehyde 5-iodovanillin 6 (300 mg, 1.08 mmol), 10% palladium/carbon (34 mg, 0.03 mmol), triphenylphosphine (34 mg, 0.13 mmol), copper iodide (12 mg, 0.06 mmol), triethylamine (329 mg, 3.0 mmol), and water were added in a 50 ml sealed tube containing a magnetic stirrer, followed by stirring for 1 hour with degassing using argon. 4-ethinyl-1,2-dimethoxybenzene (437 mg, 2.70 mmol) was added to the reaction mixture above, followed by degassing using argon for 15 minutes. The reaction mixture was stirred for 24 hours at a high temperature. Upon completion of the reaction, the mixture was extracted with ethyl acetate. The extract was washed with brine. The organic layer was separated and washed with water, dried over anhydrous magnesium sulfate, filtered, and concentrated under reduced pressure. The residue was purified by silica gel column chromatography (hexane:ethylacetate=7:3) to give the target compound as a yellow solid (360 mg, 62.5%).

$^1$H NMR (CDCl$_3$, 500 MHz) δ 10.01 (1H, s, CHO), 7.70 (1H, d, J=1.0 Hz, aromaticH), 7.49 (1H, dd, J=1.9 Hz, 8.3 Hz, aromaticH), 7.38 (1H, d, J=1.8 Hz, aromaticH), 7.36 (1H, s, aromaticH), 6.99 (1H, s, aromaticH), 6.95 (1H, d, J=8.4 Hz, aromaticH), 4.10 (3H, s, CH$_3$), 4.00 (3H, s, CH$_3$), 3.95 (3H, s, CH$_3$);

PREPARATIVE EXAMPLES 2~18

The compounds shown in Table 1 were prepared by the same manner as described in Preparative Example 1.

TABLE 1

| Preparative Example | Compound | Yield | $^1$H NMR |
|---|---|---|---|
| 2 | 7-methoxy-2-(4-methoxy-2-methylphenyl)benzofuran-5-carbaldehyde | 61.9% | δ 10.02 (1H, s, CHO), 7.81 (1H, d, J = 8.4 Hz, aromaticH), 7.72 (1H, s, aromaticH), 7.37 (1H, s, aromaticH), 6.85 (3H, d, J = 10 Hz, aromaticH), 4.09 (3H, s, CH3), 3.86 (3H, s, CH$_3$), 2.57 (3H, s, CH$_3$); |
| 3 | 7-methoxy-2-m-tolylbenzofuran-5-carbaldehyde | 31.5% | δ 10.01 (1H, s, CHO), 7.72 (2H, d, J = 1.5 Hz, aromaticH), 7.70 (1H, d, J = 8.0 Hz, aromaticH), 7.38 (1H, d, J = 0.8 Hz, aromaticH), 7.34 (1H, d, J = 7.5 Hz, aromaticH), 7.21 (1H, d, J = 7.5 Hz, aromaticH), 7.09 (1H, s, aromaticH), 4.11 (3H, s, CH$_3$), 2.44 (3H, s, CH$_3$); |
| 4 | 7-methoxy-2-p-tolylbenzofuran-5-carbaldehyde | 38.6% | δ 10.01 (1H, s, CHO), 7.80 (2H, d, J = 8.0 Hz, aromaticH), 7.71 (1H, s, aromaticH), 7.37 (1H, s, aromaticH), 7.27 (2H, d, J = 9.6 Hz aromaticH), 7.05 (1H, s, aromaticH), 4.10 (3H, s, CH$_3$), 2.41 (3H, s, CH$_3$); |
| 5 | 7-methoxy-2-(3-methoxyphenyl)benzofuran-5-carbaldehyde | 71.8% | δ 10.01 (1H, s, CHO), 7.72 (1H, d, J = 1.5 Hz, aromaticH), 7.49 (1H, d, J = 7.5 Hz, aromaticH), 7.43 (1H, t, J = 2.0 Hz, aromaticH), 7.38 (2H, t, J = 8.0 Hz aromaticH), 7.11 (1H, s, aromaticH), 6.95 (1H, dd, J = 2.0 Hz, 8.0 Hz, aromaticH), 4.10 (3H, s, CH$_3$), 3.90 (3H, s, CH$_3$); |
| 6 | 2-(3,5-difluorophenyl)-7-methoxybenzofuran-5-carbaldehyde | 14.1% | δ 10.02 (1H, s, CHO), 7.74 (1H, s, aromaticH), 7.41 (3H, d, J = 4.8 aromaticH), 7.15 (1H, s, aromaticH), 6.83 (1H, t, J = 8.8, aromaticH), 4.10 (3H, s, CH$_3$) |
| 7 | 7-methoxy-2-(4-methoxyphenyl)benzofuran-5-carbaldehyde | 80% | δ 10.01 (1H, s, CHO), 7.83 (2H, d, J = 8.0 Hz, aromaticH), 7.69 (1H, s, aromaticH), 7.34 (1H, s, aromaticH), 6.98 (2H, d, J = 8.0 Hz, aromaticH) 6.96 (1H, s, aromaticH), 4.09 (3H, s, CH$_3$), 3.87 (3H, s, CH$_3$); |
| 8 | 2-(3-fluorophenyl)-7-methoxybenzofuran-5-carbaldehyde | 77.8% | δ 10.02 (1H, s, CHO), 7.74 (1H, s, aromaticH), 7.68 (1H, d, J = 8.0 Hz, aromaticH), 7.58.7.62 (1H, m, aromaticH), 7.44 (1H, q, J = 8 Hz, aromaticH), 7.41 (1H, d, J = 8 Hz, aromaticH), 7.14 (1H, s, aromaticH), 7.09 (1H, s, aromaticH), 4.10 (1H, s, CH$_3$), 2.44 (3H, s, CH$_3$); |
| 9 | 2-(4-(dimethylamino)phenyl)-7-methoxybenzofuran-5-carbaldehyde | 45.8% | δ 9.99 (1H, s, CHO), 7.70 (2H, d, J = 8.0 Hz, aromaticH), 7.66 (1H, s, aromaticH), 7.32 (1H, s, aromaticH), 6.87 (1H, s, aromaticH), 6.76 (2H, d, J = 8.0 Hz, aromaticH), 4.09 (3H, s, CH$_3$), 3.03 (6H, s, CH$_3$); |
| 10 | 7-methoxy-2-(2-methoxyphenyl)benzofuran-5-carbaldehyde | 69.1% | δ 10.01 (1H, s, CHO), 8.13 (1H, dd, J = 1.6, 1.6 Hz, aromaticH), 7.73 (1H, d, J = 1.6 Hz, aromaticH), 7.43 (1H, s, aromaticH), 7.34-7.39 (2H, m, aromaticH), 7.07.7.11 (1H, m, aromaticH), 7.03 (1H, d, J = 8.4 Hz, aromaticH), 4.10 (3H, s, CH3), 4.02 (3H, s, CH3); |

TABLE 1-continued

| Preparative Example | Compound | Yield | $^1$H NMR |
|---|---|---|---|
| 11 | 7-methoxy-2-(3-(trifluoromethyl)phenyl)benzofuran-5-carbaldehyde | 52.1% | δ 10.02 (1H, s, CHO), 8.14 (1H, s, aromaticH), 8.07 (1H, d, J = 7.2 Hz, aromaticH), 7.75 (1H, d, J = 1.6 Hz, aromaticH), 7.62 (1H, q, J = 8 Hz aromaticH), J = 7.41 (1H, d, J = 1.2 Hz, aromaticH), 7.21 (1H, s, aromaticH), 4.11 (3H, s, CH$_3$); |
| 12 | 2-(3,5-dimethoxyphenyl)-7-methoxybenzofuran-5-carbaldehyde | 53.4% | δ 10.01 (1H, s, CHO), 7.72 (1H, d, J = 0.8 Hz, aromaticH), 7.38 (1H, s, aromaticH), 7.09 (1H, s, aromaticH), 7.04 (2H, d, J = 2.8 Hz, aromaticH), 6.51 (2H, t, J = 2.0 Hz, aromaticH), 4.10 (3H, s, CH$_3$), 3.88 (6H, s, CH$_3$). |
| 13 | 7-methoxy-2-(4-(trifluoromethyl)phenyl)benzofuran-5-carbaldehyde | 73.0% | δ 10.02 (1H, s, CHO), 8.01 (1H, d, J = 8.4, aromaticH), 7.75 (1H, d, J = 0.8 Hz, aromaticH), 7.72 (2H, d, J = 8.4, aromaticH), 7.41 (1H, d, J = 1.2 Hz aromaticH), 7.23 (1H, s, aromaticH), 4.11 (3H, s, CH$_3$); |
| 14 | 2-(4-(tert-butyldimethylsiloxy)-3-methoxyphenyl)-7-methoxybenzofuran-5-carbaldehyde | 61.9% | δ 10.00 (1H, s, CHO), 7.69 (1H, d, J = 1.6 Hz, aromatic-H), (3H, m, aromatic-H), 6.97 (1H, s, aromatic-H), 6.92 (1H, dd, J$_1$ = 0.8 Hz, J$_2$ = 1.2 Hz, aromatic-H), 4.09 (3H, s, CH$_3$), 3.92 (3H, s, CH$_3$), 1.01 (9H, t, J = 3.2 Hz, CH$_3$), 0.12 (6H, t, J = 3.2 Hz, CH$_3$); |
| 15 | 2-(3-(tert-butyldimethylsiloxy)-4-methoxyphenyl)-7-methoxybenzofuran-5-carbaldehyde | 75.2% | δ 10.00 (1H, s, CHO), 7.68 (1H, d, J = 1.2 Hz, aromatic-H), 7.49 (1H, dd, J$_1$ = 2.0 Hz, J$_2$ = 2.0 Hz, aromatic-H), 7.34 (2H, t, J = 1.6 Hz, aromatic-H), 6.93 (1H, s, aromatic-H), 6.92 (1H, d, J = 8.8 Hz, aromatic-H), 4.09 (3H, s, CH$_3$), 3.86 (3H, s, CH$_3$), 1.03 (9H, t, J = 2.8 Hz, CH$_3$), 0.20 (6H, t, J = 3.2 Hz, CH$_3$); |
| 16 | 2-(3,5-bis(tert-butyldimethylsilyloxy)phenyl)-7-methoxybenzofuran-5-carbaldehyde | 88.2% | δ10.00 (1H, s, CHO), 7.70 (1H, d, J = 1.2 Hz, aromatic-H), 7.36 (1H, d, J = 1.2 Hz, aromatic-H), 7.03 (1H, s, aromatic-H), 6.99 (2H, d, J = 2.0 Hz, aromatic-H), 6.36 (1H, t, J = 2.0 Hz, aromatic-H), 4.10 (3H, s, CH$_3$), 1.01 (18H, t, J = 3.2 Hz, CH$_3$), 0.24 (12H, t, J = 3.2 Hz, CH$_3$); |
| 17 | 2-(3,4-bis(tert-butyldimethylsilyloxy)phenyl)-7-methoxybenzofuran-5-carbaldehyde | 73.1% | δ 10.00 (1H, s, CHO), 7.68 (1H, s, aromatic-H), 7.39 (1H, dd, J$_1$ = 2.0 Hz, J$_2$ = 2.4 Hz, aromatic-H), 7.34 (1H, s, aromatic-H), 7.32 (1H, d, J = 2.0 Hz, aromatic-H), 6.89-6.91 (2H, m, aromatic-H), 4.09 (3H, s, CH$_3$), 0.99-1.03 (18H, m, CH$_3$), 0.23-0.26 (12H, m, CH$_3$); |
| 18 | 2-(4-(tert-butyldimethylsilyloxy)-3,5-dimethoxyphenyl)-7-methoxybenzofuran-5-carbaldehyde | 90.4% | δ 10.00 (1H, s, CHO), 7.69 (1H, d, J = 1.2 Hz, aromatic-H), 7.36 (1H, d, J = 1.2 Hz, aromatic-H), 7.07 (1H, s, aromatic-H), 6.99 (1H, s, aromatic-H), 4.09 (3H, s, CH$_3$), 3.90 (6H, s, CH$_3$), 1.02 (9H, t, J = 2.8 Hz, CH$_3$), 0.16 (6H, t, J = 2.8 Hz, CH$_3$); |

PREPARATIVE EXAMPLE 19

(E)-methyl-3-[2-(3,4-dimethoxyphenyl)-7-methoxybenzofuran-5-yl]acrylate 2-(3,4-dimethoxyphenyl)-7-methoxybenzofuran-5-carbaldehyde (100 mg, 0.32 mmol) prepared in Preparative Example 1 was dissolved in dichloromethane (5 mL), to which methyl(triphenylphosphoranyliden)acetate (1.07 g, 3.20 mmol) was added, followed by stirring at a high temperature for 12 hours. Upon completion of the reaction, the reaction mixture was concentrated under reduced pressure. The residue was purified by silica gel column chromatography (hexane:ethylacetate=8:2) to give the target compound as a white solid (100 mg, 85.5%).

$^1$H NMR (CDCl$_3$, 500 MHz) δ 7.77 (1H, d, J=15.5 Hz, =CH), 7.47 (1H, dd, J=1.0 Hz, 8.0 Hz, aromaticH), 7.37 (2H, d, J=1.0 Hz, aromaticH), 6.97 (1H, s, aromaticH), 6.94 (1H, d, J=8.5 Hz, aromaticH), 6.90 (1H, s, aromaticH), 6.42 (1H, d, J=15.5 Hz, =CH), 4.08 (3H, s, CH$_3$), 3.99 (3H, s, CH$_3$), 3.94 (3H, s, CH$_3$), 3.83 (3H, s, CH$_3$);

PREPARATIVE EXAMPLES 20~36

The compounds shown in Table 2 were prepared by the same manner as described in Preparative Example 19.

TABLE 2

| Preparative Example | Compound | Yield | $^1$H NMR |
|---|---|---|---|
| 20 | (E)-methyl-3-(7-methoxy-2-(4-methoxy-2-methylphenyl)benzofuran-5-yl)acrylate | 90.2% | δ 7.78 (2H, t, J = 8.4 Hz, aromaticH), 7.35 (1H, s, aromaticH), 6.97 (1H, s, aromaticH), 6.84 (2H, d, J = 6.8 Hz, aromaticH), 6.77 (1H, s, aromatic H), 6.42 (1H, d, J = 16.0 Hz, =CH), 4.07 (3H, s, CH$_3$), 3.85 (3H, s, CH$_3$), 3.82 (3H, s, CH$_3$), 2.55 (3H, s, CH$_3$); |
| 21 | (E)-methyl-3-(7-methoxy-2-m-tolylbenzofuran-5-yl)acrylate | 83% | δ 7.78 (1H, d, J = 16.0 Hz, =CH), 7.70 (2H, d, J = 17.6 Hz, aromaticH), 7.36 (2H, s, aromaticH), 7.20 (1H, s, aromaticH), 7.36 (2H, s, aromaticH), 6.42 (1H, d, J = 16.0 Hz, =CH), 4.08 (3H, s, CH$_3$), 3.82 (3H, s, CH$_3$), 2.42 (3H, s, CH$_3$); |
| 22 | (E)-methyl-3-(7-methoxy-2-p-tolylbenzofuran-5-yl)acrylate | 85% | δ 7.77 (1H, d, J = 16.0 Hz, =CH), 7.76 (1H, d, J = 8.4 Hz, aromaticH), 7.34 (1H, s, aromaticH), 6.96 (2H, d, J = 6.4 Hz, aromaticH), 6.42 (1H, d, J = 16.0 Hz, =CH), 4.08 (3H, s, CH$_3$), 3.82 (3H, s, CH$_3$), 2.40 (3H, s, CH$_3$); |
| 23 | (E)-methyl-3-(7-methoxy-2-(3-methoxyphenyl)benzofuran-5-yl)acrylate | 57.6% | δ 7.77 (1H, d, J = 16.0 Hz, =CH), 7.47 (1H, d, J = 7.5 Hz, aromaticH), 7.37-7.41 (3H, m, aromaticH), 6.98 (2H, d, J = 1.0 Hz, aromaticH), 6.92 (1H, dd, J = 2.0 Hz, 8.5 Hz, aromaticH), 6.42 (1H, d, J = 16.0 Hz, =CH), 4.08 (3H, s, CH3) 3.89 (3H, s, CH3), 3.82 (3H, s, CH3); |
| 24 | (E)-methyl-3-(2-(3,5-difluorophenyl)-7-methoxybenzofuran-5-yl)acrylate | 28.9% | δ 7.77 (1H, d, J = 16.0 Hz, =CH), 7.367.39 (3H, m, aromaticH), 7.05 (1H, s, aromaticH), 7.01 (1H, d, J = 1.0 Hz, aromaticH), 6.81 (1H, t, J = 2.0 Hz, 8.5 Hz aromaticH), 6.43 (1H, d, J = 16.0 Hz, =CH), 4.08 (3H, s, CH3), 3.83 (3H, s, CH3) |
| 25 | (E)-methyl-3-(7-methoxy-2-(4-methoxyphenyl)benzofuran-5-yl)acrylate | 60.7% | δ 7.82 (1H, s, aromaticH), 7.80 (1H, s, aromaticH), 7.76 (1H, d, J = 16.0 Hz, =CH), 7.32 (1H, s, aromaticH), 6.98 (1H, s, aromaticH), 6.96 (1H, s, aromaticH), 6.41 (1H, d, J = 16.0 Hz, =CH), 4.07 (3H, s, CH$_3$), 3.86 (3H, s, CH$_3$), 3.82 (3H, s, CH$_3$); |
| 26 | (E)-methyl-3-(2-(3-fluorophenyl)-7-methoxybenzofuran-5-yl)acrylate | 88.7% | δ 7.77 (1H, d, J = 16.0 Hz, =CH), 7.647.66 (1H, m, aromaticH), 7.567.59 (H, m, aromaticH), 7.387.44 (1H, m, aromaticH), 7.36 (1H, s, aromaticH), 7.06-7.08 (1H, m, aromaticH), 7.03 (1H, s, aromaticH), 7.00 (1H, s, aromaticH), 6.42 (1H, d, J = 16.0 Hz, =CH), 4.08 (3H, s, CH$_3$), 3.82 (3H, s, CH$_3$); |
| 27 | (E)-methyl-3-(2-(4-dimethylamino)phenyl)-7-methoxybenzofuran-5-yl)acrylate | 79.2% | δ 7.76 (1H, d, J = 16.0 Hz, =CH),, 7.70 (2H, d, J = 8.0 Hz aromaticH), 7.30 (1H, s, aromaticH), 6.93 (1H, s, aromaticH), 6.79 (3H, s, aromaticH), 6.40 (1H, d, J = 16.0 Hz, =CH), 4.07 (3H, s, CH$_3$), 3.03 (6H, s, CH$_3$); |
| 28 | (E)-methyl-3-(7-methoxy-2-(2-methoxyphenyl)benzofuran- | 53.8% | δ 8.10 (1H, dd, J = 2.0, 2.0 Hz, aromaticH), 7.77 (1H, d, J = 15.6 Hz, =CH),, 7.36 (2H, d, J = 1.6 Hz aromaticH), 7.33 (2H, dd, J = 2.8, |

TABLE 2-continued

| Preparative Example | Compound | Yield | $^1$H NMR |
|---|---|---|---|
|  | 5-yl)acrylate |  | 1.6 Hz, aromaticH), 7.05-7.09 (1H, m, aromaticH), 7.01 (1H, d, J = 10.4 aromaticH), 6.97 (1H, d, J = 1.6 aromaticH), 6.41 (1H, d, J = 16.0 Hz, =CH), 4.07 (3H, s, CH$_3$), 4.01 (3H, s, CH$_3$), 3.82 (3H, s, CH$_3$); |
| 29 | (E)-methyl-3-(7-methoxy-2-(3-(trifluoromethyl)phenyl)benzofuran-5-yl)acrylate | 86.3% | δ8.12 (1H, s, aromaticH), 7.77 (1H, d, J = 15.6 Hz, =CH), 7.59 (2H, t, J = 7.6 Hz aromaticH), 7.37 (1H, d, J = 1.2 Hz, aromaticH), 7.11 (1H, s, aromaticH), 7.01 (1H, d, J = 0.8 aromaticH), 6.43 (1H, d, J = 15.6 Hz, =CH), 4.08 (3H, s, CH$_3$), 3.83 (3H, s, CH$_3$); |
| 30 | (E)-methyl-3-(2-(3,5-dimethoxyphenyl)-7-methoxybenzofuran-5-yl)acrylate | 58.5% | δ7.77 (1H, d, J = 16 Hz, =CH), 7.35 (1H, s, aromaticH), 7.03 (2H, t, J = 1.2, aromaticH), 6.99 (2H, d, J = 8.4 Hz, aromaticH), 6.49 (1H, t, J = 2, aromaticH), 6.42 (1H, d, J = 15.5 Hz, =CH), 4.07 (3H, s, CH$_3$), 3.87 (6H, s, CH$_3$), 3.82 (3H, s, CH$_3$) |
| 31 | (E)-methyl-3-(7-methoxy-2-(4-(trifluoromethyl)phenyl)benzofuran-5-yl)acrylate | 87.2% | δ7.98 (2H, d, J = 8.0 Hz aromaticH), 7.77 (1H, d, J = 16.0 Hz, =CH), 7.70 (2H, t, J = 8 Hz aromaticH), 7.38 (1H, d, J = 1.6 Hz, aromaticH), 7.13 (1H, s, aromaticH), 7.02 (1H, d, J = 1.2 aromaticH), 6.43 (1H, d, J = 15.6 Hz, =CH), 4.08 (3H, s, CH3), 3.83 (3H, s, CH3); |
| 32 | (E)-methyl-3-(2-4(tert-butyldimethylsilyloxy)-3-methoxyphenyl)-7-methoxybenzofuran-5-yl)acrylate | 67% | δ 7.76 (1H, d, J = 16.0 Hz, =CH), 7.32-7.36 (3H, m, aromatic-H), 6.96 (1H, d, J = 1.6 Hz aromatic-H), 6.91 (1H, d, J = 8.8 Hz, aromatic-H), 6.88 (1H, s, aromatic H), 6.41 (1H, d, J = 16.0 Hz, =CH), 4.07 (3H, s, CH$_3$), 3.91 (3H, s, CH$_3$), 3.82 (3H, s, CH$_3$), 1.01 (9H, t, J = 3.2 Hz, CH$_3$), 0.18 (6H, t, J = 3.2 Hz, CH$_3$); |
| 33 | (E)-methyl-3-(2-(3-(tert-butyldimethlysilyloxy)-4-methoxyphenyl)-7-methoxybenzofuran-5-yl)acrylate | 81.9% | δ 7.76 (1H, d, J = 16.0 Hz, =CH), 7.47 (1H, dd, J$_1$ = 2.0 Hz, J$_2$ = 2.0 Hz, aromatic-H), 7.32 (1H, d, J = 2.4 Hz aromatic-H), 7.31 (1H, d, J = 1.2 Hz, aromatic-H), 6.95 (1H, d, J = 1.2 Hz, aromatic-H), 6.91 (1H, d, J = 8.8 Hz aromatic-H), 6.84 (1H, s, aromatic H), 6.41 (1H, d, J = 16.0 Hz, =CH), 4.07 (3H, s, CH$_3$), 3.85 (3H, s, CH$_3$), 3.82 (3H, s, CH$_3$), 1.03 (9H, t, J = 2.8 Hz, CH$_3$), 0.20 (6H, t, J = 3.2 Hz, CH$_3$); |
| 34 | (E)-methyl-3-(2-(3,5-bis(tert-butyldimethylsilyloxy)phenyl)-7-methoxybenzofuran-5-yl)acrylate | 84.2% | δ 7.76 (1H, d, J = 16.0 Hz, =CH), 7.33 (1H, d, J = 0.8 H, aromatic-H), 6.97 (3H, d, J = 2.0 Hz, aromatic-H), 6.94 (1H, s, aromatic-H), 6.41 (1H, d, J = 16.0 Hz, =CH), 6.35 (1H, t, J = 2.0 Hz, aromatic-H), 4.08 (3H, s, CH$_3$), 3.82 (3H, s, CH$_3$), 1.00 (18H, t, J = 2.8 Hz, CH$_3$), 0.24 (12H, t, J = 3.2 Hz, CH$_3$); |
| 35 | (E)-methyl-3-(2-(3,4-bis(tert-butyldimethylsilyloxy)phenyl)-7-methoxybenzofuran-5-yl)acrylate | 77.8% | δ7.76 (1H, d, J = 16.0 Hz, =CH), 7.37 (1H, dd, J = 1.6 H, J = 2.0 H, aromatic-H), 7.31 (1H, d, J = 1.2 Hz aromatic-H), 7.30 (1H, d, J = 2.0 H, aromatic-H), 6.95 (1H, d, J = 1.6 H, aromatic-H), 6.89 (1H, d, J = 8.4 H, aromatic-H), 6.81 (1H, s, aromatic-H), 6.41 (1H, d, J = 16.4 Hz, =CH), 6.35 (1H, t, J = 2.0 Hz, aromatic-H), 4.07 (3H, s, CH$_3$), 3.82 (3H, s, CH$_3$), |

TABLE 2-continued

| Preparative Example | Compound | Yield | ¹H NMR |
|---|---|---|---|
| 36 | (E)-methyl-3-(2-(4-(tert-butyldimethylsilyloxy)-3,5-dimethoxyphenyl)-7-methoxybenzofuran-5-yl)acrylate | 66.3% | 0.99-1.03 (18H, m, CH$_3$), 0.22-0.25 (12H, m, CH$_3$); δ 7.77 (1H, d, J = 16.0 Hz, =CH), 7.32 (1H, d, J = 1.2 H, aromatic-H), 7.05 (2H, s, aromatic-H), 6.96 (1H, d, J = 1.2 H, aromatic-H), 6.89 (1H, s, aromatic-H), 6.42 (1H, d, J = 16.0 Hz, =CH), 4.07 (3H, s, CH$_3$), 3.89 (6H, s, CH$_3$), 3.82 (3H, s, CH$_3$), 1.02 (9H, d, J = 3.2 Hz, CH$_3$), 0.16 (6H, t, J = 3.2 Hz, CH$_3$); |

PREPARATIVE EXAMPLE 37

Methyl 3-(2-(3,4-dimethoxyphenyl)-7-methoxybenzofuran-5-yl)propanoate (E)-methyl-3-[2-(3,4-dimethoxyphenyl)-7-methoxybenzofuran-5-yl]acrylate (50 mg, 0.14 mmol) prepared in Preparative Example 14 was dissolved in tetrahydrofuran (5 mL), to which palladium/carbon (29 mg, 0.014 mmol, 10 wt %) was added with a couple of drops of acetic acid, followed by stirring at room temperature for 30 minutes. Upon completion of the reaction, the mixture was concentrated under reduced pressure. The residue was purified by silica gel column chromatography (hexane:ethylacetate=7:3) to give the target compound as a white solid (48 mg, 95.4%).

¹H NMR (CDCl$_3$, 400 MHz) δ 7.45 (1H, dd, J=2.0 Hz, J=2.0 Hz, aromaticH), 7.36 (1H, d, J=2.0 Hz, aromaticH), 6.98 (1H, s, aromaticH), 6.92 (1H, d, J=8.0 Hz, aromaticH), 6.63 (1H, d, J=1.2, aromaticH), 4.06 (3H, s, CH$_3$), 3.94 (3H, s, CH$_3$), 3.91 (3H, s, CH$_3$), 3.68 (3H, s, CH$_3$), 3.02 (2H, t, J=8, CH$_2$), 2.68 (2H, t, J=8, CH$_2$);

PREPARATIVE EXAMPLE 38~54

The compounds shown in Table 3 were prepared by the same manner as described in Preparative Example 37.

TABLE 3

| Preparative Example | Compound | Yield | ¹H NMR |
|---|---|---|---|
| 38 | methyl-3-(7-methoxy-2-(4-methoxy-2-methylphenyl)benzofuran-5-yl)propanoate | 98.8% | δ7.77 (1H, d, J = 9.6 Hz, aromaticH), 7.00 (1H, s, aromaticH), 6.84 (2H, t, J = 9.6 Hz, aromaticH), 6.72 (1H, s, aromaticH), 6.64 (1H, s, aromaticH), 4.03 (3H, s, CH$_3$), 3.84 (3H, s, CH$_3$), 3.69 (3H, s, CH$_3$), 4.02 (2H, t, J = 8 Hz, CH$_2$). 2.68(2H, t, J = 8 Hz, CH$_2$), 2.54(3H, s, CH$_3$); |
| 39 | methyl-3-(7-methoxy-2-m-tolylbenzofuran-5-yl)propanoate | 99% | δ7.70 (1H, s, aromaticH), 7.66 (2H, d, J = 8 Hz, aromaticH), 7.31 (1H, t, J = 8 Hz, aromaticH), 7.15 (1H, d, J = 8 Hz, aromaticH) 6.99 (1H, s, aromaticH), 6.93 (1H, s, aromaticH), 4.04 (3H, s, CH$_3$), 3.02 (2H, t, J = 8 Hz, CH$_2$), 2.68 (2H, t, J = 8 Hz, CH$_2$), 2.41(3H, s, CH$_3$); |
| 40 | methyl-3-(7-methoxy-2-p-tolylbenzofuran-5-yl)propanoate | 100% | δ7.76 (2H, d, J = 8 Hz aromaticH), 7.23 (2H, d, J = 8 Hz aromaticH), 6.98 (1H, s, aromaticH), 6.89 (1H, s, aromaticH) 6.63 (1H, s, aromaticH) 4.03 (3H, s, CH$_3$), 3.68 (3H, s, CH$_3$), 3.02 (2H, t, J = 8 Hz, CH$_2$), 2.68 (2H, t, J = 8 Hz, CH$_2$), 2.38(3H, s, CH$_3$); |
| 41 | methyl-3-(7-methoxy-2-(3-methoxyphenyl)benzofuran-5-yl)propanoate | 89.5% | δ7.46 (2H, d, J = 8 Hz, aromaticH), 7.40 (1H, s, aromaticH), 7.34 (1H, t, J = 8 Hz, aromaticH), 7.00 (1H, s, aromaticH) 6.94 (1H, s, aromaticH) 6.89 (1H, q, J = 8 Hz, aromaticH), 6.65 (1H, s, aromaticH), 4.03 (3H, s, CH3), 3.88 (3H, s, CH3),). 2.38(3H, s, CH$_3$) 3.02 (2H, t, J = 8 Hz, |

TABLE 3-continued

| Preparative Example | Compound | Yield | $^1$H NMR |
|---|---|---|---|
| | | | CH$_2$), 2.68 (2H, t, J = 8 Hz, CH2); |
| 42 | methyl-3-(2-(3,5-difluorophenyl)-7-methoxybenzofuran-5-yl)propanoate | 89.5% | δ7.34-7.38 (2H, m, aromaticH), 7.01 (2H, d, J = 1.2 Hz, aromaticH), 6.98 (1H, s, aromaticH), 6.75-6.80 (1H, m, aromaticH), 6.68 (1H, d, J = 1.6 Hz, aromaticH,) 4.03 (3H, s, CH$_3$), 3.68 (3H, s, CH$_3$), 3.03 (2H, t, J = 8 Hz, CH$_2$), 2.68 (2H, t, J = 8 Hz, CH$_2$); |
| 43 | methyl-3-(7-methoxy-2-(4-methoxyphenyl)benzofuran-5-yl)propanoate | 87.9% | δ7.80 (2H, q, J = 4 Hz aromaticH), 7.65-6.98 (2H, m, aromaticH), 6.81 (1H, s, aromaticH), 6.62 (1H, s, aromaticH), 4.03 (3H, s, CH$_3$), 3.85 (3H, s, CH$_3$), 3.68 (3H, s, CH$_3$), 3.02 (2H, t, J = 8 Hz, CH$_2$), 2.68 (2H, t, J = 8 Hz, CH$_2$); |
| 44 | methyl-3-(2-(3-fluorophenyl)-7-methoxybenzofuran-5-yl)propanoate | 80.3% | δ7.64 (1H, d, J = 8 Hz, aromaticH), 7.54-7.58 (1H, m, aromaticH), 7.36-7.41 (1H, m, aromaticH), 7.04 (1H, q, J = 4 Hz, aromaticH) 7.01 (1H, s, aromaticH), 6.97 (1H, s, aromaticH), 6.67 (1H, d, J = 4 Hz, aromaticH,) 4.03 (3H, s, CH$_3$), 3.68 (3H, s, CH$_3$), 3.02 (2H, t, J = 8 Hz, CH$_2$), 2.68 (2H, t, J = 8 Hz, CH$_2$); |
| 45 | methyl-3-(2-(4-(dimethylamino)phenyl)-7-methoxybenzofuran-5-yl)propanoate | 67.6% | δ7.74 (2H, d, J = 8 Hz aromaticH), 6.94 (1H, s, aromaticH), 6.75 (2H, d, J = 8 Hz aromaticH), 6.72 (1H, s, aromaticH), 6.59 (1H, s, aromaticH), 4.03 (3H, s, CH$_3$), 3.68 (3H, s, CH$_3$), 3.01 (2H, t, J = 8 Hz, CH$_2$), 3.01 (6H, s, CH$_3$), 2.67 (2H, t, J = 8 Hz, CH$_2$); |
| 46 | methyl-3-(7-methoxy-2-(2-methoxyphenyl)benzofuran-5-yl)propanoate | 86.6% | δ8.10 (1H, dd, J = 1.6, 1.6 Hz aromaticH), 7.29-7.34 (1H, m, aromaticH), 7.28 (1H, s, aromaticH), 7.06 (1H, t, J = 7.6 Hz aromaticH), 7.00 (2H, d, J = 8.4 Hz aromaticH), 6.64 (1H, d, J = 1.2 Hz aromaticH), 4.04 (3H, s, CH$_3$), 4.00 (3H, s, CH$_3$), 3.68 (3H, s, CH$_3$), 3.02 (2H, t, J = 8 Hz, CH$_2$), 2.68 (2H, t, J = 8 Hz, CH$_2$); |
| 47 | methyl-3-(7-methoxy-2-(3-(trifluoromethyl)phenyl)benzofuran-5-yl)propanoate | 68.2% | δ8.10 (1H, dd, J = 1.6, 1.6 Hz aromaticH), 8.03 (1H, d, J = 7.2 Hz aromaticH), 7.57 (1H, t, J = 7.6 Hz aromaticH), 7.04 (1H, s, aromaticH), 7.02 (1H, d, J = 0.08 Hz aromaticH), 6.68 (1H, s, aromaticH), 4.04 (3H, s, CH$_3$), 3.69 (3H, s, CH$_3$), 3.03 (2H, t, J = 8 Hz, CH$_2$), 2.69 (2H, t, J = 8 Hz, CH$_2$); |
| 48 | methyl-3-(2-(3,5-dimethoxyphenyl)-7-methoxybenzofuran-5-yl)propanoate | 87.2% | δ7.02 (2H, d, J = 2.4 Hz, aromaticH), 7.00 (1H, s, aromaticH), 6.93 (1H, s, aromaticH), 6.65 (1H, d, J = 1.2 Hz, aromaticH), 6.46 (1H, t, J = 2.4, aromaticH), 4.03 (3H, s, CH$_3$), 3.86 (6H, s, CH$_3$), 3.68 (3H, s, CH$_3$), 3.02 (2H, t, J = 8, CH$_2$), 2.68 (2H, t, J = 8, CH$_2$); |
| 49 | methyl-3-(7-methoxy-2-(4-(trifluoromethyl)phenyl)benzofuran-5-yl)propanoate | 68.2% | δ7.97 (2H, d, J = 8.4 Hz, aromaticH), 7.68 (2H, d, J = 8.4 Hz, aromaticH), 7.07 (1H, s, aromaticH), 7.03 (1H, d, J = 1.2 Hz, aromaticH), 6.69 (1H, d, J = |

TABLE 3-continued

| Preparative Example | Compound | Yield | $^1$H NMR |
|---|---|---|---|
| | | | 1.2 Hz aromaticH), 4.04 (3H, s, CH$_3$), 3.68 (3H, s, CH$_3$), 3.03 (2H, t, J = 8 Hz, CH$_2$), 2.69 (2H, t, J = 8 Hz, CH$_2$); |
| 50 | methyl-3-(2-(4-(tert-butyldimethylsilyloxy)-3-methoxyphenyl)-7-methoxybenzofuran-5-yl)propanoate | 96.4% | δ 7.32-7.34 (2H, m, aromatic-H), 6.97 (1H, d, J = 0.8 Hz, aromatic-H), 6.89 (1H, d, J = 8.0 Hz, aromatic-H), 6.81 (1H, s, aromatic-H), 6.21 (1H, d, J = 1.2 Hz, aromatic-H), 4.03 (3H, s, CH$_3$), 3.90 (3H, s, CH$_3$), 3.68 (3H, s, CH$_3$), 3.01 (2H, t, J = 8.4 Hz, —CH$_2$). 2.68(2H, t, J = 7.6 Hz, CH$_2$), 2.54(3H, s, CH$_3$), 1.00 (9H, t, J = 3.2 Hz, CH$_3$), 0.18 (6H, t, J = 2.8 Hz, CH$_3$); |
| 51 | methyl-3-(2-(3-(tert-butyldimethylsilyloxy)-4-methoxyphenyl)-7-methoxybenzofuran-5-yl)propanoate | 90.5% | δ 7.45 (1H, dd, J$_1$ = 2.0 Hz, J$_2$ = 2.4 Hz, aromatic-H), 7.31 (1H, d, J = 2.4 Hz, aromatic-H), 6.96 (1H, d, J = 0.8 Hz, aromatic-H), 6.89 (1H, d, J = 8.4 Hz, aromatic-H), 6.61 (1H, d, J = 1.2 Hz, aromatic-H), 4.03 (3H, s, CH$_3$), 3.84 (3H, s, CH$_3$), 3.68 (3H, s, CH$_3$), 3.01 (2H, t, J = 8 Hz, —CH$_2$). 2.67(2H, t, J = 8 Hz, CH$_2$), 1.02 (9H, t, J = 2.8 Hz, CH$_3$), 0.19 (6H, t, J = 3.2 Hz, CH$_3$); |
| 52 | methyl-3-(2-(3,5-bis(tert-butyldimethylsilyloxy)phenyl)-7-methoxybenzofuran-5-yl)propanoate | 90.4% | δ 6.98 (1H, s, aromatic-H), 6.96 (2H, d, J = 1.6 Hz, aromatic-H), 6.63 (1H, s, aromatic-H), 6.32 (1H, t, J = 2.0 Hz, aromatic-H), 4.04 (3H, s, CH$_3$), 3.68 (3H, s, CH$_3$), 3.01 (2H, t, J = 8.0 Hz, —CH$_2$). 2.68(2H, t, J = 8.0 Hz, CH$_2$), 1.00 (18H, d, J = 2.4 Hz, CH$_3$), 0.23 (12H, t, J = 3.2 Hz, CH$_3$); |
| 53 | methyl-3-(2-(3,4-bis(tert-butyldimethylsilyloxy)phenyl)-7-methoxybenzofuran-5-yl)propanoate | 83.3% | δ 7.35 (1H, dd, J = 2.0 Hz, J = 2.4 Hz, aromatic-H), 7.28 (1H, d, J = 2.0 Hz, aromatic-H), 6.96 (1H, d, J = 1.2 Hz, aromatic-H), 6.32 (1H, d, J = 8.4 Hz, aromatic-H), 6.75 (1H, s, aromatic-H), 6.61 (1H, d, J = 1.2 Hz, aromatic-H), 4.04 (3H, s, CH$_3$), 3.68 (3H, s, CH$_3$), 3.01 (2H, t, J = 8.0 Hz, —CH$_2$). 2.67(2H, t, J = 8.0 Hz, CH$_2$), 0.94-1.02 (18H, m, CH$_3$), 0.21-0.25 (12H, m, CH$_3$); |
| 54 | methyl-3-(2-(4-(tert-butyldimethylsilyloxy)-3,5-dimethoxyphenyl)-7-methoxybenzofuran-5-yl)propanoate | 79.2% | δ 6.96 (2H, s, aromatic-H), 6.97 (1H, d, J = 0.8 Hz, aromatic-H), 6.83 (1H, s, aromatic-H), 6.62 (1H, d, J = 1.2 Hz, aromatic-H), 4.02 (3H, s, CH$_3$), 3.88 (6H, s, CH$_3$), 3.68 (3H, s, CH$_3$), 3.02 (2H, t, J = 8.0 Hz, —CH$_2$). 2.68(2H, t, J = 8.0 Hz, CH$_2$), 1.01 (9H, t, J = 2.4 Hz, CH$_3$), 0.15 (6H, t, J = 3.2 Hz, CH$_3$); |

PREPARATIVE EXAMPLE 55

Methyl-3-(3-(3,4-dimethoxyphenethyl)-4-hydroxy-5-methoxyphenyl)propanoate (E)-methyl-3-[2-(3,4-dimethoxyphenyl)-7-methoxybenzofuran-5-yl]acrylate prepared in Preparative Example 14 was dissolved in tetrahydrofuran (5 mL), to which palladium/carbon (0.5 equivalent, 5 weight %) was added, followed by stirring at room temperature in the presence of hydrogen for 10 hours. Upon completion of the reaction, the mixture was filtered with celite and concentrated under reduced pressure. The residue was purified by silica gel column chromatography (hexane:ethylacetate=7:3) to give the target compound as a white solid.

$^1$H NMR (CDCl$_3$, 400 MHz) δ 6.79 (1H, d, J=8.0 Hz, aromaticH), 6.75 (1H, d, J=8.0 Hz, aromaticH), 6.72 (1H, d, J=2.0 Hz, aromaticH), 6.58 (1H, d, J=2.0 Hz, aromaticH), 6.53 (1H, d, J=1.6 Hz, aromaticH), 5.58 (1H, s, OH), 3.87

(3H, s, CH$_3$), 3.86 (3H, s, CH$_3$), 3.85 (3H, s, CH$_3$),3.67 (3H, s, CH$_3$), 2.82-2.89 (6H, m, CH$_2$), 2.57 (2H, t, J=8.0 Hz, CH$_2$).

PREPARATIVE EXAMPLE 56

Methyl-3-(4-hydroxy-3-methoxy-5-(3-methylpentethyl)phenyl)propanoate

The target compound was obtained as a white solid (291.2 mg, 96.5%) by the same manner as described in Preparative Example 55 except that methyl-3-(7-methoxy-2-p-tolylbenzofuran-5-yl)propanoate prepared in Preparative Example 40 was used.

$^1$H NMR (CDCl$_3$, 400 MHz) δ 7.17 (1H, s, aromaticH), 7.03 (3H, d, J=14.4 Hz, aromaticH), 6.58 (1H, s, aromaticH), 6.55 (1H, s, aromaticH), 5.57 (1H, s, OH), 3.87 (3H, s, CH$_3$), 3.67 (3H, s, CH$_3$), 2.86 (6H, s, CH$_2$), 2.57 (2H, s, CH$_2$), 2.33(3H, s, CH$_3$).

PREPARATIVE EXAMPLE 57

Methyl-3-(4-hydroxy-3-methoxy-5-(4-methylpentethyl)phenyl)propanoate

The target compound was obtained as a white solid (28.3 mg, 67%) by the same manner as described in Preparative Example 55 except that methyl-3-(7-methoxy-2-m-tolylbenzofuran-5-yl)propanoate prepared in Preparative Example 39 was used.

$^1$H NMR (CDCl$_3$, 400 MHz) δ 7.76 (4H, s, aromaticH), 6.58 (1H, s, aromaticH), 6.52 (1H, s, aromaticH), 5.56 (1H, s, OH), 3.87 (3H, s, CH$_3$), 3.67 (3H, s, CH$_3$), 2.86 (6H, s, CH$_2$), 2.56 (2H, s, CH$_2$), 2.32 (3H, s, CH$_3$).

PREPARATIVE EXAMPLE 58

Methyl-3-(4-hydroxy-3-methoxy-5-(3-methoxypentethyl)phenyl)propanoate

The target compound was obtained as a white solid (154.5 mg, 69.8%) by the same manner as described in Preparative Example 55 except that methyl-3-(7-methoxy-2-(3-methoxyphenyl)benzofuran-5-yl)propanoate prepared in Preparative Example 41 was used.

$^1$H NMR (CDCl$_3$, 400 MHz) δ 7.20 (1H, s, aromaticH), 6.83 (1H, s, aromaticH), 6.76 (2H, s, aromaticH), 6.58 (1H, s, aromaticH), 6.52 (1H, s, aromaticH), 5.57 (1H, s, OH), 3.87 (3H, s, CH$_3$), 3.79 (3H, s, CH$_3$), 3.67 (3H, s, CH$_3$), 2.85 (6H, d, J=16 Hz, CH$_2$), 2.56 (2H, s, CH$_2$).

PREPARATIVE EXAMPLE 59

2-(3,4-dimethoxyphenyl)-7-methoxy-5-vinylbenzofuran 2-(3,4-dimethoxyphenyl)-7-methoxybenzofuran-5-carbaldehyde (60 mg, 0.19 mmol) prepared in Preparative Example 1 and methyltriphenylphosphonium iodine (116 mg, 0.29 mmol) were dissolved in dimethylformamide (5 mL), to which sodium hydride (0.023 g, 0.95 mmol) was added at 0° C., followed by stirring at room temperature for 12 hours. The reaction mixture was extracted with ethyl acetate and brine. The organic layer was separated and washed with water, dried over anhydrous magnesium sulfate, filtered, and concentrated under reduced pressure. The residue was purified by silica gel column chromatography (hexane:ethylacetate=7:3) to give the target compound as a white solid (0.05 mg, 83.3%).

$^1$H NMR (CD$_3$OD, 500 MHz) δ 7.47 (1H, dd, J=2.0 Hz, 8.0 Hz, aromatic-H), 7.44 (1H, d, J=2.0 Hz, aromatic-H), 7.18 (1H, s, aromatic-H), 7.04 (1H, d, J=8.5 Hz, aromatic-H), 7.02 (1H, s, aromatic-H), 6.98 (1H, s, aromatic-H), 6.79 (1H, dd, J=10.5 Hz, 17.5 Hz, —CH═), 5.74 (1H, d, J=17.5 Hz, trans-CH═), 5.18 (1H, d, J=11.0 Hz, cis-CH═), 4.04 (3H, s, CH3), 3.93 (3H, s, CH3), 3.88 (3H, s, CH3);

PREPARATIVE EXAMPLE 60

7-methoxy-2-(4-methoxy-2-methylphenyl)-5-vinylbenzofuran

The target compound was obtained (0.055 g, 91.6%) by the same manner as described in Preparative Example 44 except that 7-methoxy-2-(4-methoxy-2-methylphenyl)benzofuran-5-carbaldehyde (60 mg, 0.20 mmol) prepared in Preparative Example 2 was used instead of 2-(3,4-dimethoxyphenyl)-7-methoxybenzofuran-5-carbaldehyde.

$^1$H NMR (CD$_3$OD, 400 MHz) δ 7.79 (1H, d, J=8 Hz, aromaticH), 7.20 (1H, d, J=1.2 Hz, aromaticH), 6.90 (1H, d, J=1.2 Hz, aromaticH), 6.746.90 (4H, m, aromaticH, ═CH), 5.71 (1H, d, J=17.6 Hz, ═CH$_2$), 5.22 (1H, d, J=11.2 Hz, ═CH$_2$), 4.06 (3H, s, CH$_3$), 3.84 (3H, s, CH$_3$), 3.88 (3H, s, CH$_3$), 2.54 (3H, s, CH$_3$);

PREPARATIVE EXAMPLES 61~65

The compounds shown in Table 4 were prepared by the same manner as described in Example 1.

TABLE 4

| Preparative Example | Compound | Yield | $^1$H NMR |
|---|---|---|---|
| 61 | 3-(2-(4-(tert-butyldimethylsiloxy)-3-methoxyphenyl)-7-methoxybenzofuran-5-yl)propane-1-ol | 89.1% | δ 7.32-7.35 (2H, m, aromatic-H), 6.98 (1H, d, J = 0.8 Hz, aromatic-H), 6.89 (1H, d, J = 3.2 Hz, aromatic-H), 6.81 (1H, s, aromatic-H), 6.63 (1H, s, aromatic-H), 4.04 (3H, s, CH$_3$), 3.90 (3H, s, CH$_3$), 3.72 (2H, q, J = 12.0 Hz, CH$_2$), 2.78 (2H, t, J = 3.6 Hz, CH$_2$), 1.92-1.99 (2H, m, CH$_2$), 1.01 (9H, d, J = 2.4 Hz, CH$_3$), 0.19 (6H, t, J = 2.4 Hz, CH$_3$); |
| 62 | 3-(2-(3-(tert-butyldimeth- | 87.1% | δ 7.46 (1H, dd, J$_1$ = 2.0 Hz, J$_2$ = 2.4 Hz, aromatic-H), 7.32 (1H, |

TABLE 4-continued

| Preparative Example | Compound | Yield | ¹H NMR |
|---|---|---|---|
| | ylsiloxy)-4-methoxyphenyl)-7-methoxybenzofuran-5-yl)propane-1-ol | | d, J = 2.4 Hz, aromatic-H), 6.96 (1H, d, J = 0.8 Hz, aromatic-H), 6.89 (1H, d, J = 8.4 Hz, aromatic-H), 6.77 (1H, s, aromatic-H), 6.62 (1H, d, J = 1.2 Hz, aromatic-H), 4.04 (3H, s, CH₃), 3.84 (3H, s, CH₃), 3.71 (2H, q, J = 12.0 Hz, CH₂), 2.77 (2H, t, J = 7.6 Hz, CH₂), 1.91-1.98 (2H, m, CH₂), 1.02 (9H, d, J = 2.8 Hz, CH₃), 0.19 (6H, t, J = 2.4 Hz, CH₃); |
| 63 | 3-(2-(3,5-bis(tert-butyldimeth-ylsilyloxy)phenyl)-7-methoxybenzofuran-5-yl)propane-1-ol | 94.7% | δ 6.98 (1H, d, J = 1.2 Hz, aromatic-H), 6.97 (1H, d, J = 2.4 Hz, aromatic-H), 6.87 (1H, s, aromatic-H), 6.65 (1H, d, J = 1.6 Hz, aromatic-H), 6.32 (1H, t, J = 2.0 Hz, aromatic-H), 4.04 (3H, s, CH₃), 3.71 (2H, d, J = 4.0 Hz, CH₂), 2.78 (2H, t, J = 3.6 Hz, CH₂), 1.91-1.98 (2H, m, CH₂), 1.00 (18H, t, J = 5.4 Hz, CH₃), 0.23 (12H, t, J = 3.2 Hz, CH₃); |
| 64 | 3-(2-(3,4-bis(tert-butyldimeth-ylsilyloxy)phenyl)-7-methoxybenzofuran-5-yl)propane-1-ol | 81.9% | δ 7.035 (1H, dd, J = 2.0 Hz, J = 2.0 Hz, aromatic-H), 7.29 (1H, d, J = 2.4 Hz, aromatic-H), 6.96 (1H, s, aromatic-H), 6.87 (1H, d, J = 8.4 Hz, aromatic-H), 6.75 (1H, s, aromatic-H), 6.62 (1H, d, J = 1.2 Hz, aromatic-H), 4.04 (3H, s, CH₃), 3.71 (2H, d, J = 4.0 Hz, CH₂), 2.77 (2H, t, J = 3.6 Hz, CH₂), 1.91-1.98 (2H, m, CH₂), 0.97-1.02 (18H, m, CH₃), 0.21-0.25 (12H, m, CH₃); |
| 65 | 3-(2-(4-(tert-butyldimeth-ylsilyloxy)-3,5-dimethoxyphenyl)-7-methoxybenzofuran-5-yl)propane-1-ol | 82.4% | δ 7.04 (2H, s, aromatic-H), 6.98 (1H, d, J = 1.2 Hz, aromatic-H), 6.83 (1H, s, aromatic-H), 6.34 (1H, d, J = 1.6 Hz, aromatic-H), 4.04 (3H, s, CH₃), 3.88 (6H, s, CH₃), 3.72 (2H, t, J = 2.4 Hz, CH₂), 2.78 (2H, t, J = 8.0 Hz, CH₂), 1.93-1.99 (2H, m, CH₂), 1.02 (9H, t, J = 3.2 Hz, CH₃), 0.15 (9H, t, J = 3.2 Hz, CH₃); |

PREPARATIVE EXAMPLE 66

2-(3,4-dimethoxyphenyl)-7-hydroxybenzofuran-5-carbaldehyde 3,4-dihydroxy-5-iodobenzaldehyde (250 mg, 0.96 mmol), 10% palladium/carbon (34 mg, 0.03 mmol), triphenylphosphine (34 mg, 0.13 mmol), copper iodide (12 mg, 0.06 mmol), triethylamine (329 mg, 3.0 mmol), and water were added in a 50 ml sealed tube containing a magnetic stirrer, followed by stirring for 1 hour with degassing using argon. 4-ethinyl-1,2-dimethoxybenzene (437 mg, 2.70 mmol) was added to the reaction mixture, followed by degassing with argon gas for 15 minutes. Then, the mixture was stirred at a high temperature for 24 hours. Upon completion of the reaction, the reaction mixture was extracted with ethyl acetate and the extract was washed with brine. The organic layer was separated and washed with water, dried over anhydrous magnesium sulfate, filtered, and concentrated under reduced pressure. The residue was purified by silica gel column chromatography (hexane:ethylacetate=5:5) to give the target compound as a yellow solid (120 mg, 40%).

¹H NMR (CD₃OD, 400 MHz) δ 9.91 (1H, s, CHO), 7.66 (1H, d, J=1.2 Hz, aromatic-H), 7.29-7.55 (1H, m, aromatic-H), 7.25 (1H, d, J=0.8 Hz, aromatic-H), 7.18 (1H, s, aromatic-H), 7.07 (1H, d, J=7.6 Hz aromatic-H), 3.94 (3H, s, CH₃), 3.89 (3H, s, CH₃);

PREPARATIVE EXAMPLE 67

(E)-methyl-3-(2-(3,4-dimethoxyphenyl)-7-hydroxy-benzofuran-5-yl)acrylate 2-(3,4-dimethoxyphenyl)-7-hydroxybenzofuran-5-carbaldehyde (110 mg, 0.37 mmol) prepared in Preparative Example 66 was dissolved in dichloromethane (5 mL), to which methyl(triphenylphosphoranyliden)acetate (308 mg, 0.92 mmol) was added, followed by stirring at a high temperature for 12 hours. Upon completion of the reaction, the reaction mixture was concentrated under reduced pressure. The residue was purified by silica gel column chromatography (hexane:ethylacetate=7:3) to give the target compound as a white solid (70 mg, 54%).

¹H NMR (CD₃OD, 400 MHz) δ 7.65 (1H, d, J=15.6 Hz, =CH), 7.45-7.48 (2H, m, aromatic-H), 7.38 (1H, s, aromatic-H), 7.29 (1H, s, aromatic-H), 7.07 (1H, d, J=8.0 Hz, aromatic-H), 7.01 (1H, d, J=1.2 Hz, aromatic-H), 6.44 (1H, d, J=16.0 Hz, =CH), 3.85 (3H, s, CH₃), 3.80 (3H, s, CH₃), 3.71 (3H, s, CH₃);

PREPARATIVE EXAMPLE 68

Methyl-3-(2-(3,4-dimethoxyphenyl)-7-hydroxybenzofuran-5-yl)propanoate (E)-methyl-3-(2-(3,4-dimethoxyphenyl)-7-hydroxybenzofuran-5-yl)acrylate (60 mg, 0.17 mmol) prepared in Preparative Example 67 was dissolved in tetrahydrofuran (5 mL), to which palladium/carbon (29 mg, 0.014 mmol, 10 wt %) was added with a couple of drops of acetic acid, followed by stirring at room temperature for 30 minutes in the presence of hydrogen. Upon completion of the reaction, the reaction mixture was concentrated under reduced pressure. The residue was purified by silica gel column chromatography (hexane:ethylacetate=7:3) to give the target compound as a white solid (56 mg, 93.3%).

$^1$H NMR (CD₃OD, 400 MHz) δ 9.99 (1H, s, aromatic-OH), 7.43 (1H, dd, $J_1$=1.6 Hz, $J_2$=2.0 Hz, aromatic-H), 7.41 (1H, m, d, J=2.0 Hz, aromatic-H), 7.17 (1H, s, aromatic-H), 7.06 (1H, d, J=8.4 Hz, aromatic-H), 6.84 (1H, d, J=0.8 Hz, aromatic-H), 6.56 (1H, d, J=1.2 Hz, aromatic-H), 3.85 (3H, s, CH₃), 3.79 (3H, s, CH₃), 3.57 (3H, s, CH₃), 2.82 (2H, t, J=3.6 Hz, CH₂), 2.61 (2H, t, J=3.6 Hz, CH₂);

EXAMPLE 1

3-[2-(3,4-dimethoxyphenyl)-7-methoxybenzofuran-5-yl]propane-1-ol

Methyl 3-(2-(3,4-dimethoxyphenyl)-7-methoxybenzofuran-5-yl]propanoate (57 mg, 0.15 mmol) prepared in Preparative Example 27 was dissolved in tetrahydrofuran (5 mL), to which lithium aluminum hydride (2.0 M, 0.15 mL, 0.31 mmol) dissolved in tetrahydrofuran was slowed added at 0° C., followed by stirring until the completion of the reaction was confirmed with thin layer chromatography. Upon completion of the reaction, 10% HCl was added to the mixture, and ethyl acetate and brine were also added thereto. The organic layer was separated and washed with water, dried over anhydrous magnesium sulfate, filtered, and concentrated under reduced pressure. The residue was purified by silica gel column chromatography (hexane:ethylacetate=5:5) to give the target compound as a white solid (46 mg, 87.5%).

$^1$H NMR (CDCl₃, 400 MHz) δ 7.45 (1H, dd, J=2.0 Hz, 8.5 Hz, aromaticH), 7.37 (1H, d, J=2.0 Hz, aromaticH), 6.98 (1H, d, J=1.2 Hz aromaticH), 6.93 (1H, d, J=8.4 Hz, aromaticH), 6.84 (1H, s, aromaticH), 6.64 (1H, d, J=1.2 Hz, aromaticH), 4.04 (3H, s, CH₃), 3.99 (3H, s, CH₃), 3.93 (3H, s, CH₃), 3.72 (2H, q, J=5.6 Hz, CH₂), 2.79 (2H, t, J=8 Hz, CH₂), 1.92.1.99 (2H, m, CH₂);

EXAMPLES 2~13

The compounds shown in Table 5 were prepared by the same manner as described in Example 1.

TABLE 5

| Example | Compound | Yield | $^1$H NMR |
|---|---|---|---|
| 2 | 3-(7-methoxy-2-(4-methoxy-2-methylphenyl)benzofuran-5-yl)propane-1-ol | 89.1% | δ7.78 (1H, d, J = 2.0 Hz, 7.2 Hz, aromaticH), 7.01 (1H, d, J = 1.2 Hz, aromaticH), 6.826.84 (2H, m, aromaticH), 6.72 (1H, s, aromaticH), 6.65 (1H, d, J = 1.2 Hz, aromaticH), 4.04 (3H, s, CH₃), 3.84 (3H, s, CH₃), 3.72 (2H, d, J = 5.2 Hz, 6.0 Hz, CH₂), 2.81 (2H, t, J = 7.6 Hz, CH₂), 1.922.04 (2H, m, CH₂); |
| 3 | 3-(7-methoxy-2-m-tolylbenzofuran-5-yl)propane-1-ol | 50% | δ7.71 (1H, s, aromaticH) 7.66 (1H, d, J = 8 Hz, aromaticH), 7.31, (1H, t, J = 8 Hz, aromaticH), 7.15 (1H, d, J = 8 Hz , aromaticH), 7.00 (1H, s, aromaticH), 6.93 (1H, s, aromaticH), 6.65 (1H, s, aromaticH), 4.05 (3H, s, CH₃), 3.71 (2H, q, J = 8 Hz, CH₂), 2.79 (2H, t, J = 8 Hz, CH₂), 2.41 (3H, s, CH₃), 1.931.97 (2H, m, CH₂), 0.88 (1H, t, J = 8 Hz, OH) |
| 4 | 3-(7-methoxy-2-p-tolylbenzofuran-5-yl)propane-1-ol | 80.3% | δ7.76 (2H, d, J = 8.0 Hz, aromaticH), 7.23 (2H, d, J = 8 Hz, aromaticH), 6.99 (1H, s, aromaticH), 6.89 (1H, s, aromaticH), 6.64 (1H, s, aromaticH), 4.04 (3H, s, CH₃), 3.71 (2H, q, J = 8 Hz, CH₂), 2.78 (2H, t, J = 8 Hz, CH₂), 2.39 (3H, s, CH₃), 1.911.98 (2H, m, CH₂), 1.27 (1H, t, J = 8 Hz, OH), |
| 5 | 3-(7-methoxy-2-(3-methoxyphenyl)benzofuran-5-yl)propane-1-ol | 75.8% | δ7.46 (1H, d, J = 8 Hz, aromaticH), 7.40 (1H, s, aromaticH), 7.34 (1H, t, J = 8 Hz, aromaticH), 7.00 (1H, s, aromaticH), 6.95 (1H, s, aromaticH) 6.89 (1H, q, J = 8 Hz, aromaticH), 6.66 (1H, s, aromaticH), 4.04 (3H, s, CH₃), 3.89 (3H, s, CH₃),). 3.71 (2H, q, |

TABLE 5-continued

| Example | Compound | Yield | $^1$H NMR |
|---|---|---|---|
| | | | J = 8 Hz, CH$_2$), 2.79 (2H, t, J = 8 Hz, CH$_2$), 1.93-1.99 (2H, m, CH$_2$), 1.27 (1H, t, J = 8 Hz, OH), |
| 6 | 3-[2-(3,5-difluorophenyl)-7-methoxybenzofuran-5-yl]propane-1-ol | 28.5% | δ7.39 (1H, d, J = 2.0 Hz, aromaticH), 7.36 (1H, d, J = 2.0 Hz, aromaticH), 7.02 (1H, s, aromaticH), 6.98 (1H, s, aromaticH), 6.77 (1H, t, J = 2.0 Hz, 6.8 Hz, aromaticH), 6.70 (1H, s, aromaticH), 4.04 (3H, s, CH$_3$), 3.72 (2H, q, J = 6.0 Hz, CH$_2$), 2.79 (2H, t, J = 7.5 Hz, CH$_2$), 1.88-2.04 (2H, m, CH$_2$); |
| 7 | 3-(7-methoxy-2-(4-methoxyphenyl)benzofuran-5-yl)propane-1-ol | 73.8% | δ7.79 (2H, t, J = 8.0 Hz, aromaticH), 6.99 (2H, d, J = 4 Hz, aromaticH), 6.96 (2H, d, J = 4 Hz, aromaticH), 6.84 (1H, s, aromaticH), 6.63 (1H, s, aromaticH), 4.04 (3H, s, CH$_3$), 3.85 (3H, s, CH$_3$), 3.71 (2H, q, J = 8 Hz, CH$_2$), 2.78 (2H, t, J = 8 Hz, CH$_2$), 1.91-1.98 (2H, m, CH$_2$), 1.26 (1H, t, J = 8 Hz, OH); |
| 8 | 3-(2-(3-fluorophenyl)-7-methoxybenzofuran-5-yl)propane-1-ol | 95.8% | δ7.64 (1H, d, J = 8 Hz, aromaticH) 7.57 (1H, d, J = 8 Hz, aromaticH), 7.39, (1H, q, J = 8 Hz, aromaticH), 7.01-7.05 (2H, m, aromaticH), 6.97 (1H, s, aromaticH), 4.04 (3H, s, CH$_3$), 3.72 (2H, q, J = 8 Hz, CH$_2$), 2.79 (2H, t, J = 8 Hz, CH$_2$), 1.91-1.99 (2H, m, CH$_2$), 1.27 (1H, q, J = 8 Hz, OH); |
| 9 | 3-(2-(4-(dimethylamino)phenyl)-7-methoxybenzofuran-5-yl)propane-1-ol | 78.6% | δ7.74 (2H, d, J = 8.0 Hz, aromaticH), 6.95 (2H, s, aromaticH), 6.75 (2H, d, J = 8 Hz, aromaticH), 6.72 (1H, s, aromaticH), 6.59 (1H, s, aromaticH), 4.04 (3H, s, CH$_3$), 3.71 (2H, q, J = 8 Hz, CH$_2$), 3.01 (6H, s, CH$_3$), 2.77 (2H, t, J = 8 Hz, CH$_2$), 1.91-1.98 (2H, m, CH$_2$), 1.265(1H, t, J = 8 Hz, OH); |
| 10 | 3-(7-methoxy-2-(2-methoxyphenyl)benzofuran-5-yl)propane-1-ol | 85% | δ8.10 (1H, dd, J = 1.6, 1.6 Hz aromaticH), 7.297.31 (1H, m, aromaticH), 7.25 (1H, d, J = 0.8 Hz, aromaticH), 7.06 (1H, t, J = 8 Hz, aromaticH), 7.01 (2H, dd, J = 0.8, 8.4 Hz aromaticH), 6.64 (1H, s, aromaticH), 4.04 (3H, s, CH$_3$), 3.99 (3H, s, CH$_3$), 3.71 (2H, q, J = 8 Hz, CH$_2$), 2.78 (2H, t, J = 8 Hz, CH$_2$), 1.91-1.97 (2H, m, CH$_2$), 0.885 (1H, t, J = 8 Hz, OH); |
| 11 | 3-(7-methoxy-2-(3-(trifluoromethyl)phenyl)benzofuran-5-yl)propane-1-ol | 79.4% | δ8.10 (1H, s, aromaticH) 8.03 (1H, d, J = 7.2 Hz, aromaticH), 7.52-7.59 (2H, m, aromaticH), 7.03 (2H, d, J = 6.4 Hz, aromaticH), 6.69 (1H, d, J = 1.2 Hz, aromaticH), 4.05 (3H, s, CH$_3$), 3.72 (2H, d, J = 2.4 Hz, CH$_2$), 2.80 (2H, t, J = 8 Hz, CH$_2$), 1.92-1.99 (2H, m, CH$_2$), 1.28(1H, d, J = 29.2 Hz, OH); |
| 12 | 3-[2-(3,5-dimethoxyphenyl)-7-methoxybenzofuran-5-yl]propane-1-ol | 90.1% | δ7.02 (1H, d, J = 2.0 Hz, aromaticH), 7.00 (1H, d, J = 1.2 Hz, aromaticH), 6.93 (1H, s, aromaticH), 6.66 (1H, d, J = 0.8 Hz, aromaticH), 6.46 (1H, t, J = 3.0 Hz, aromaticH), 4.04 (3H, s, CH$_3$), 3.86 (6H, s, CH$_3$), 3.72 (2H, q, J = 5.2 Hz, CH$_2$), 2.78 (2H, t, J = 8 Hz, CH$_2$), 1.91-1.98 (2H, m, CH$_2$), 1.31 (1H, t, J = 4.8 Hz, OH) |
| 13 | 3-(7-methoxy-2-(4-(trifluoromethyl)phe- | 79.4% | δ7.97 (2H, d, J = 8.8 Hz, aromaticH) 7.67 (2H, d, J = 8.4 Hz, aromaticH), 7..06 (1H, s, |

| Example | Compound | Yield | $^1$H NMR |
|---|---|---|---|
| | nyl)benzofuran-5-yl)propane-1-ol | | aromaticH), 7.03 (1H, s, aromaticH), 6.69 (1H, d, J = 1.2 Hz, aromaticH), 4.04 (3H, s, $CH_3$), 3.72 (2H, d, J = 6.4 Hz, $CH_2$), 2.80 (2H, t, J = 8 Hz, $CH_2$), 1.921.99 (2H, m, $CH_2$), 1.35(1H, s, OH); |

EXAMPLE 14

2-(3,4-dimethoxyphenethyl)-4-(3-hydroxypropyl)-6-methoxyphenol

Methyl-3-(3-(3,4-dimethoxyphenethyl)-4-hydroxy-5-methoxyphenyl)propanoate (50 mg) prepared in Preparative Example 55 was dissolved in tetrahydrofuran (3 mL), to which lithium aluminum hydride (2.0 M, 1.0 equivalent) dissolved in tetrahydrofuran was slowed added at 0° C., followed by stirring until the completion of the reaction was confirmed with thin layer chromatography. Upon completion of the reaction, 10% HCl was added to the mixture. The reaction mixture was extracted with ethyl acetate and brine. The organic layer was separated and washed with water, dried over anhydrous magnesium sulfate, filtered, and concentrated under reduced pressure. The residue was purified by silica gel column chromatography to give the target compound as a white solid (38 mg, 83.5%).

$^1$H NMR (CDCl$_3$, 500 MHz) δ 7.45 (1H, dd, J=2.0 Hz, 8.5 Hz, aromaticH), 7.37 (1H, d, J=2.0 Hz, aromaticH), 6.98 (1H, s, aromaticH), 6.93 (1H, d, J=8.5 Hz, aromaticH), 6.84 (1H, s, aromaticH), 6.64 (1H, d, J=0.5 Hz, aromaticH), 4.04 (3H, s, CH$_3$), 3.99 (3H, s, CH$_3$), 3.93 (3H, s, CH$_3$), 3.72 (2H, t, J=6.5 Hz, CH$_2$), 2.79 (2H, t, J=7.5 Hz, CH$_2$), 1.931.98 (2H, m, CH$_2$);

EXAMPLE 15

4-(3-hydroxypropyl)-2-methoxy-6-(3-methylpenethyl)phenol

The target compound was obtained (246 mg, 92.5%) by the same manner as described in Example 14 except that methyl-3-(4-hydroxy-3-methoxy-5-(3-methylpenethyl)phenyl)propanoate prepared in Preparative Example 56 was used instead of methyl-3-(3-(3,4-dimethoxyphenethyl)-4-hydroxy-5-methoxyphenyl)propanoate.

$^1$H NMR (CDCl$_3$, 400 MHz) δ 7.17 (1H, J=8 Hz, aromaticH) 7.056.99 (3H, m, aromaticH), 6.58 (1H, s, aromaticH), 6.53 (1H, s, aromaticH), 5.55 (1H, s, OH), 3.87 (3H, s, CH$_3$), 3.693.62 (2H, m, CH$_2$), 2.87 (4H, q, J=12 Hz, CH$_2$). 2.60 (2H, t, J=8 Hz, CH$_2$) 2.33 (3H, s, CH$_3$), 1.871.80 (2H, m, CH$_2$), 0.88 (1H, t, J=8Hz, OH).

Example 16

4-(3-hydroxypropyl)-2-methoxy-6-(4-methylpenethyl)phenol

The target compound was obtained as a white solid (79.7 mg, 67.3%) by the same manner as described in Example 14 except that methyl-3-(4-hydroxy-3-methoxy-5-(4-methylpenethyl)phenyl)propanoate prepared in Preparative Example 57 was used instead of methyl-3-(3-(3,4-dimethoxyphenethyl)-4-hydroxy-5-methoxyphenyl)propanoate.

$^1$H NMR (CDCl$_3$, 400 MHz) δ 7.12-7.07 (4H, m, aromaticH), 6.57 (1H, s, aromaticH), 6.52 (1H, s, aromaticH), 5.54 (1H, s, OH), 3.87 (3H, s, CH$_3$), 3.63 (2H, q, J=18 Hz, CH$_2$), 2.872 (4H, s, CH$_2$), 2.59 (2H, t, J=8 Hz, CH$_2$), 2.31 (3H, s, CH$_3$), 1.86-1.80 (2H, m, CH$_2$), 1.18 (1H, t, J=8Hz, OH).

EXAMPLE 17

4-(3-hydroxypropyl)-2-methoxy-6-(3-methoxypenethyl)phenol

The target compound was obtained as a white solid (130 mg, 92.5%) by the same manner as described in Example 14 except that methyl-3-(4-hydroxy-3-methoxy-5-(3-methoxypenethyl)phenyl)propanoate prepared in Preparative Example 58 was used instead of methyl-3-(3-(3,4-dimethoxyphenethyl)-4-hydroxy-5-methoxyphenyl)propanoate.

$^1$H NMR (CDCl$_3$, 400 MHz) δ 7.19 (1H, t, J=8Hz, aromaticH), 6.82 (1H, d, J=8 Hz, aromaticH), 6.74 (2H, d, J=12 Hz, aromaticH), 6.58 (1H, s, aromaticH), 6.51 (1H, s, aromaticH), 5.55 (1H, s, OH), 3.87 (3H, s, CH$_3$), 3.78 (3H, s, CH$_3$), 3.65 (2H, q, J=16 Hz, CH$_2$), 2.89 (4H, s, CH$_2$), 2.59 (2H, t, J=8 Hz, CH$_2$), 1.861.79 (2H, m, CH$_2$), 1.23 (1H, t, J=10 Hz, OH).

EXAMPLE 18

[2-(3,4-dimethoxyphenyl)-7-methoxybenzofuran-5-yl]methanol 2-(3,4-dimethoxyphenyl)-7-methoxybenzofuran-5-carbaldehyde (0.1 g, 0.32 mmol) prepared in Preparative Example 1 was dissolved in tetrahydrofuran (5 mL), to which sodium borohydride (0.036 g, 0.96 mmol) was added at 0° C., followed by stirring until the completion of the reaction was confirmed with thin layer chromatography. Upon completion of the reaction, 10% HCl was added to the mixture. The reaction mixture was extracted with ethyl acetate and brine. The organic layer was separated and washed with water, dried over anhydrous magnesium sulfate, filtered, and concentrated under reduced pressure. The residue was purified by silica gel column chromatography (hexane:ethylacetate=6:4) to give the target compound as a white solid (85 mg, 84.6%).

$^1$H-NMR (CDCl$_3$, 500 MHz) δ 7.50 (1H, dd, J=2.0 Hz, 8.0 Hz, aromatic-H), 7.47 (1H, d, J=1.5 Hz, aromatic-H), 7.15 (1H, s, aromatic-H), 7.12 (1H, s, aromatic-H), 7.07 (1H, d, J=8.5 Hz, aromatic-H), 6.92 (1H, s, aromatic-H), 4.68 (2H, d, J=6.0 Hz, CH$_2$), 4.14 (1H, t, J=6.0 Hz, OH), 4.02 (3H, s CH$_3$), 3.92 (3H, s, CH$_3$) 3.87 (3H, s, CH$_3$);

EXAMPLE 19

(7-methoxy-2-(4-methoxy-2-methylphenyl)benzofuran-5-yl)methanol

The target compound was obtained as a white solid by the same manner as described in Example 18 except that 7-methoxy-2-(4-methoxy-2-methylphenyl)benzofuran-5-carbaldehyde (0.1 g, 0.35 mmol) prepared in Preparative Example 2 was used instead of 2-(3,4-dimethoxyphenyl)-7-methoxybenzofuran-5-carbaldehyde (0.1 g, 0.32 mmol).

$^1$H-NMR (CDCl$_3$, 400 MHz) δ 7.80 (1H, d, J=8.0 Hz, aromatic-H), 7.17 (1H, s, aromatic-H), 6.83 (13H, d, J=8.8 Hz, aromatic-H), 6.75 (1H, s, aromatic-H), 4.76 (2H, d, J=6.0 Hz, CH$_2$), 4.05 (3H, s, CH$_3$), 3.85 (3H, s, CH$_3$), 2.55 (3H, s, CH$_3$), 2.64 (1H, t, J=12.4 Hz, OH);

EXAMPLE 20

2-[2-(3,4-dimethoxyphenyl)-7-methoxybenzofuran-5-yl]ethanol 2-(3,4-dimethoxyphenyl)-7-methoxy-5-vinylbenzofuran (30 mg, 0.10 mmol) prepared in Preparative Example 59 was dissolved in tetrahydrofuran (2 mL), to which borane tetrahydrofuran complex (1.0 M, 0.11 mL, 0.11 mmol) dissolved in tetrahydrofuran was added at 0° C., followed by stirring at room temperature for 3 hours. Then, 0.1 ml of 10% NaOH solution and 0.1 ml of 30% H$_2$O$_2$ were added thereto, followed by stirring at room temperature for 30 minutes and stirring at 55° C. for 1 hour. Upon completion of the reaction, the reaction mixture was extracted with ethyl acetate and brine. The organic layer was separated and washed with water, dried over anhydrous magnesium sulfate, filtered, and concentrated under reduced pressure. The residue was purified by silica gel column chromatography (hexane:ethylacetate=5:5) to give the target compound as a white solid (0.014 g, 43.8%).

$^1$H NMR (CD$_3$OD, 500 MHz) δ 7.46 (1H, dd, J=2.0 Hz, 8.5 Hz, aromaticH), 7.44 (1H, d, J=2.0 Hz, aromaticH), 7.03 (1H, d, J=8.0 Hz, aromaticH), 7.01 (1H, s, aromaticH), 6.98 (1H, s, aromaticH), 6.74 (1H, d, J=0.5 Hz, aromaticH), 4.01 (3H, s, CH$_3$), 3.92 (3H, s, CH$_3$), 3.87 (3H, s, CH$_3$), 3.79 (2H, t, J=7.0 Hz, CH$_2$OH), 2.88 (2H, t, J=7.0 Hz, CH$_2$);

EXAMPLE 21

2-(7-methoxy-2-(4-methoxy-2-methylphenyl)benzofuran-5-yl]ethanol

The target compound was obtained as a white solid (0.016 g, 50.1%) by the same manner as described in Example 20 except that 7-methoxy-2-(4-methoxy-2-methylphenyl)-5-vinylbenzofuran prepared in Preparative Example 60 was used instead of 2-(3,4-dimethoxyphenyl)-7-methoxy-5-vinylbenzofuran.

$^1$H NMR (CD$_3$OD, 400 MHz) δ 7.78 (1H, d, J=9.6 Hz, aromaticH), 7.04 (1H, s, aromaticH), 6.83 (2H, d, J=7.6 Hz, aromaticH), 6.71 (1H, s, aromaticH), 6.66 (1H, d, J=1.2 Hz aromaticH), 4.04 (3H, s, CH$_3$), 3.91 (2H, s, CH$_2$), 3.84 (3H, s, CH$_3$), 2.95 (2H, t, J=6.4 Hz, CH$_2$), 2.54 (3H, s, CH$_3$);

EXAMPLE 22

4-(5-(3-hydroxypropyl)-7-methoxybenzofuran-2-yl)-2-methoxyphenol 3-(2-(4-(tert-butyldimethylsiloxy)-3-methoxyphenyl)-7-methoxybenzofuran-5-yl)propane-1-ol (70 mg, 0.16 mmol) prepared in Preparative Example 61 was dissolved in tetrahydrofuran (5 mL), to which tetrabutylammonium fluoride (0.32 mmol) was added at 0° C., followed by stirring at room temperature for 30 minutes. Upon completion of the reaction, the reaction mixture was concentrated under reduced pressure. The residue was purified by silica gel column chromatography (hexane:ethylacetate=5:5) to give the target compound as a white solid (45 mg, 86.1%).

$^1$H NMR (CD$_3$OD, 400 MHz) δ 7.39 (1H, dd, J$_1$=2.0 Hz, J$_2$=2.0 Hz, aromatic-H), 7.37 (1H, d, J=1.2 Hz, aromatic-H), 6.97 (2H, d, J=7.6 Hz, aromatic-H), 6.81 (1H, s, aromatic-H), 6.63 (1H, s, aromatic-H), 4.03 (3H, s, CH3), 3.99 (3H, s, CH3), 3.71 (2H, t, J=6.4 Hz, CH2), 2.78 (2H, t, J=3.6 Hz, CH2), 1.91-1.98 (2H, m, CH2);

EXAMPLE 23

5-(5-(3-hydroxypropyl)-7-methoxybenzofuran-2-yl)-2-methoxyphenol

The target compound was obtained (40 mg, 67.8%) by the same manner as described in Example 22 except that 3-(2-(3-(tert-butyldimethylsiloxy)-3-methoxyphenyl)-7-methoxybenzofuran-5-yl)propane-1-ol prepared in Preparative Example 62 was used instead of 3-(2-(4-(tert-butyldimethylsiloxy)-3-methoxyphenyl)-7-methoxybenzofuran-5-yl)propane-1-ol.

$^1$H NMR (CD$_3$OD, 400 MHz) δ 7.35 (1H, dd, J$_1$=2.4 Hz, J$_2$=1.6 Hz, aromatic-H), 7.30 (1H, d, J=2.0 Hz, aromatic-H), 7.00 (1H, d, J=8.4 Hz, aromatic-H), 6.97 (1H, d, J=0.8 Hz, aromatic-H), 6.88 (1H, s, aromatic-H), 6.70 (1H, s, aromatic-H), 4.01 (3H, s, CH$_3$), 3.90 (3H, s, CH$_3$), 3.59 (2H, t, J=7.6 Hz, CH$_2$), 2.74 (2H, t, J=8.0 Hz, CH$_2$), 1.86-1.90 (2H, m, CH$_2$);

EXAMPLE 24

5-(5-(3-hydroxypropyl)-7-methoxybenzofuran-2-yl)benzene-1,3-diol

The target compound was obtained (90 mg, 85.5%) by the same manner as described in Example 22 except that 3-(2-(3,5-bis(tert-butyldimethylsilyloxy)phenyl)-7-methoxybenzofuran-5-yl)propane-1-ol prepared in Preparative Example 63 was used instead of 3-(2-(4-(tert-butyldimethylsiloxy)-3-methoxyphenyl)-7-methoxybenzofuran-5-yl)propane-1-ol.

$^1$H NMR (CD$_3$OD, 400 MHz) δ 7.35 (2H, s, OH), 7.12 (1H, s, aromatic-H), 6.97 (1H, s, aromatic-H), 6.74 (1H, s, aromatic-H), 6.72 (1H, d, J=2.4 Hz, aromatic-H), 6.22 (1H, t, J=2.4 Hz, aromatic-H), 4.46 (1H, t, J=4.8 Hz, OH), 3.93 (3H, s, CH$_3$), 3.42 (2H, q, J=6.4 Hz, CH$_2$), 2.65 (2H, t, J=8.0 Hz, CH$_2$), 1.71-1.78 (2H, m, CH$_2$);

EXAMPLE 25

4-(5-(3-hydroxypropyl)-7-methoxybenzofuran-2-yl)benzene-1,2-diol

The target compound was obtained (70 mg, 74.5%) by the same manner as described in Example 22 except that 3-(2-(3,4-bis(tert-butyldimethylsilyloxy)phenyl)-7-methoxybenzofuran-5-yl)propane-1-ol prepared in Preparative Example 64 was used instead of 3-(2-(4-(tert-butyldimethylsiloxy)-3-methoxyphenyl)-7-methoxybenzofuran-5-yl)propane-1-ol.

¹H NMR (CD₃OD, 400 MHz) δ 7.12 (1H, d, J=2.0 Hz, aromatic-H), 7.16 (1H, dd, J=2.0 Hz, J=2.0 Hz, aromatic-H), 6.98 (1H, s, aromatic-H), 6.94 (1H, s, aromatic-H), 6.81 (1H, d, J=8.4 Hz, aromatic-H), 6.71 (1H, s, aromatic-H), 3.94 (3H, s, $CH_3$), 3.43 (2H, t, J=6.8 Hz, $CH_2$), 2.66 (2H, t, J=8.0 Hz, $CH_2$), 1.71-1.78 (2H, m, $CH_2$);

EXAMPLE 26

4-(5-(3-hydroxypropyl)-7-methoxybenzofuran-2-yl)-2,6-dimethoxyphenol

The target compound was obtained (80 mg, 74.8%) by the same manner as described in Example 22 except that 3-(2-(4-(tert-butyldimethylsilyloxy)-3,5-dimethoxyphenyl)-7-methoxybenzofuran-5-yl)propane-1-ol prepared in Preparative Example 65 was used instead of 3-(2-(4-(tert-butyldimethylsiloxy)-3-methoxyphenyl)-7-methoxybenzofuran-5-yl)propane-1-ol.

¹H NMR (CD₃OD, 400 MHz) δ 8.79 (1H, s, OH), 7.21 (1H, s, aromatic-H), 7.10 (2H, s, aromatic-H), 6.96 (1H, s, aromatic-H), 6.74 (1H, d, J=1.2 Hz, aromatic-H), 6.22 (1H, t, J=2.4 Hz, aromatic-H), 4.47 (1H, s, OH), 4.03 (3H, s, $CH_3$), 3.86 (6H, s, $CH_3$), 3.44 (2H, t, J=6.4 Hz, $CH_2$), 2.67 (2H, t, J=8.0 Hz, $CH_2$), 1.73-1.80 (2H, m, $CH_2$);

EXAMPLE 27

2-(3,4-dimethoxyphenethyl)-5-(3-hydroxypropyl)-7-ol

Methyl-3-(2-(3,4-dimethoxyphenyl)-7-hydroxybenzofuran-5-yl)propanoate (56 mg, 0.16 mmol) prepared in Preparative Example 68 was dissolved in tetrahydrofuran (5 mL), to which lithium aluminum hydride (2.0 M, 0.15 mL, 0.31 mmol) dissolved in tetrahydrofuran was slowed added at 0° C., followed by stirring until the completion of the reaction was confirmed with thin layer chromatography. Upon completion of the reaction, 10% HCl was added to the mixture, and ethyl acetate and brine were also added thereto. The organic layer was separated and washed with water, dried over anhydrous magnesium sulfate, filtered, and concentrated under reduced pressure. The residue was purified by silica gel column chromatography (hexane:ethylacetate=5:5) to give the target compound as a white solid (36 mg, 67.9%).

¹H NMR (CD₃OD, 400 MHz) δ 9.88 (1H, s, aromatic-OH), 7.43 (1H, dd, $J_1$=1.6 Hz, $J_2$=2.0 Hz, aromatic-H), 7.41 (1H, m, d, J=2.0 Hz, aromatic-H), 7.16 (1H, s, aromatic-H), 7.06 (1H, d, J=8.4 Hz, aromatic-H), 6.81 (1H, d, J=0.8 Hz, aromatic-H), 6.55 (1H, d, J=1.2 Hz, aromatic-H), 3.85 (3H, s, $CH_3$), 3.79 (3H, s, $CH_3$), 3.36-3.44 (2H, m, $CH_2$), 2.57 (2H, t, J=8.4 Hz, $CH_2$), 1.67-1.74 (2H, m, $CH_2$);

EXAMPLE 28

3-(2-(3,4-dimethoxyphenyl)-7-methoxybenzofuran-5-yl)propyl acetate

3-[2-(3,4-dimethoxyphenyl)-7-methoxybenzofuran-5-yl]propane-1-ol (50 mg, 0.09 mmol) prepared in Example 1 was dissolved in dichloromethane (5 mL), to which triethylamine was added, followed by stirring for 10 minutes. The mixture was added with acetylchloride at 0° C., followed by stirring at room temperature for 12 hours. Then, the reaction mixture was concentrated under reduced pressure. The residue was purified by silica gel column chromatography (hexane:ethylacetate=6:4) to give the target compound as a white solid (40 mg, 71%).

¹H NMR (CD₃OD, 400 MHz) δ 7.45 (1H, dd, J=2.0 Hz, J=2.0 Hz, aromatic-H), 7.36 (1H, d, J=2.0 Hz, aromatic-H), 6.96 (1H, d, J=1.2 Hz, aromatic-H), 6.93 (1H, d, J=8.4 Hz, aromatic-H), 6.84 (1H, s, aromatic-H), 6.61 (1H, d, J=1.2 Hz, aromatic-H), 4.13 (2H, d, J=6.8 Hz, $CH_2$), 4.04 (3H, s, $CH_3$), 3.99 (3H, s, $CH_3$), 3.93 (3H, s, $CH_3$), 2.76 (2H, d, J=7.6 Hz, $CH_2$), 2.07 (3H, s, $CH_3$), 1.97-2.04 (2H, m, $CH_2$),

EXPERIMENTAL EXAMPLE 1

Evaluation of Cell Survival Rate of Macrophages

Raw 264.7 (ATCC TIB71) cells, the mouse derived macrophages', were inoculated in a 96-well plate containing DMEM (Dulbecco's modified Eagle medium; Welgene, Korea) supplemented with 10% FBS (Fetal Bovine Serum), 2 mM glutamine, penicillin (100 unit/ml), and streptomycin (100 μg/ml) at the density of $1\times10^4$ cells/well. The cells were cultured in 5% $CO_2$ at 37° C. for 4 hours to attach the cells onto the plate. Next, the cells were treated with each sample at different concentrations, followed by further culture for 24 hours. To investigate the cell survival rate, 5 mg/ml of MTT (3-(4,5-dimethylthiazol-2-yl)-2,5-diphenyltetrazoliumbromide, Amresco, OH, USA) was distributed thereto (10 μl/well), followed by culture for 4 hours. Then, the supernatant was eliminated. Formazan reduced from MTT by mitochondria was dissolved in 100 μl of DMSO and then $OD_{570}$ was measured. 0.2% DMSO was used for the negative control. Considering OD of the negative control as 100%, the cell survival rate was calculated and presented in Table 6.

TABLE 6

| Example | Grades of cell survival rate (%, in 10 μM) |
|---|---|
| 1 | A |
| 2 | A |
| 3 | A |
| 4 | A |
| 5 | A |
| 6 | A |
| 7 | A |
| 8 | A |
| 9 | A |
| 14 | C |
| 15 | A |
| 16 | A |
| 17 | B |
| 18 | A |
| 20 | B |
| 22 | A |
| 23 | B |
| 24 | A |
| 25 | A |
| 26 | A |
| 27 | B |
| 28 | A |

(As shown in Table 6, the cell survival rate (%) at the sample concentration of 10 μM was measured and sorted by the following grades:
A: 90<A≤100;
B: 80<B≤90; and
C: 70<C≤80.)

As shown in Table 6, when the 2-phenylbenzofuran derivative of the present invention was treated at the concentration of 10 μM, the cell survival rate (%) was excellent, indicating that it has a low effect on macrophages, in other words it has low cytotoxicity to macrophages, so that it can be effectively used as a pharmaceutical composition for preventing or treating inflammatory disease.

EXPERIMENTAL EXAMPLE 2

Effect of the Compound on the Inflammation Induced Macrophages

1. Inhibition of Nitrogen Oxide (NO) Generation

Raw 264.7 (ATCC TIB71) cells were inoculated in a 96-well plate containing the same medium as used in Experimental Example 1 at the density of $1 \times 10^5$ cells/well. The cells were cultured in 5% $CO_2$ at 37° C. for 4 hours to attach the cells onto the plate. The cells were treated with each sample at different concentrations, followed by further culture for 1 hour. Inflammation induced macrophages (LPS) were treated thereto at the final concentration of 500 ng/ml, followed by further culture for 24 hours. 100 μl of the supernatant was taken and transferred in a new plate, which was mixed with Griess reagent (a mixture of 1% sulfanilamide, 0.1% N-[1-naphthyl]-ethylenediamine dihydrochloride, and 5% phosphoric acid), followed by reaction for 10 minutes. Then, $OD_{540}$ was measured. NO generation was quantified by using the sodium nitrite standard curve prepared from sodium nitrates dissolved in the same medium at different concentrations. Considering the NO generation of the inflammation induced macrophages as 100%, the NO generation inhibition rate was calculated and presented in Table 7.

TABLE 7

| Example | Grades of NO generation inhibition rate (%) |
|---|---|
| 1 | D |
| 2 | A |
| 3 | A |
| 4 | B |
| 5 | C |
| 6 | B |
| 7 | D |
| 8 | C |
| 9 | C |
| 14 | C |
| 15 | A |
| 16 | C |
| 17 | C |
| 18 | C |
| 20 | A |
| 22 | A |
| 23 | C |
| 24 | A |
| 25 | A |
| 26 | A |
| 27 | D |
| 28 | B |

(As shown in Table 7, the NO generation inhibition rate (%) according to the compounds of Examples was measured and sorted by the following grades:
A: 35<A≤100;
B: 25<B≤35;
C: 15<C≤25; and
D: 5<D≤15.)

As shown in Table 7, the 2-phenylbenzofuran derivatives of the present invention display at least 30% of NO generation inhibition rate, indicating that the derivatives are excellent in suppressing NO generation, so that they can be effectively used as a pharmaceutical composition for preventing or treating inflammatory disease.

2. Inhibition of interleukin-6 (IL-6) Generation

Raw 264.7 cells were distributed by the same manner as described in Experimental Example <2-1>, and IL-6 included in the supernatant treated with each sample at different concentrations was measured by enzyme-linked immunosorbent assay (IL-6 ELISA kit, BD Bioscience, San Diego, Calif.).

Particularly, 10-fold diluted supernatant was distributed in a 96-well plate on which IL-6 antibody was attached, followed by adhesion for 2 hours. The supernatant remaining after the adhesion was washed with a washing buffer. The detection antibody and HRP were adhered on the washed plate for 1 hour. The remaining antibody was washed. Color development was induced by using TMB substrate. The reaction was terminated with sulfuric acid solution. Then, $OD_{450}$ was measured. IL-6 in the supernatant was quantified by using the standard curve made with the standard IL-6 included in the kit. IL-6 suppression rate was calculated by measuring the same concentration that could inhibit IL-6 generation up to 50% in the LPS treated group and the results are shown in Table 8.

TABLE 8

| Example | Grades of $IC_{50}$ on IL-6 generation (μM) |
|---|---|
| 1 | B |
| 2 | A |
| 3 | E |
| 4 | A |
| 5 | E |
| 6 | B |
| 7 | E |
| 8 | E |
| 9 | E |
| 14 | N.D. |
| 15 | C |
| 16 | D |
| 17 | E |
| 18 | E |
| 20 | C |
| 22 | A |
| 23 | E |
| 24 | B |
| 25 | A |
| 26 | A |
| 27 | C |
| 28 | C |

(As shown in Table 8, $IC_{50}$ (μM) on IL-6 generation according to the compounds of Examples was measured and sorted by the following grades:
A: A≤10;
B: 10<B≤20;
C: 20<C≤30;
D: 30<D≤40; and
E: 40<E≤50.)

As shown in Table 8, the 2-phenylbenzofuran derivatives of the present invention can inhibit interleukin-6 (IL-6) generation at a low concentration, indicating that the derivatives are excellent in suppressing IL-6 generation, so that they can be effectively used as a pharmaceutical composition for preventing or treating inflammatory disease.

3. Inhibition of Tumor Necrosis Factor Alpha (TNF-alpha)

Raw 264.7 cells were distributed by the same manner as described in Experimental Example <2-1>, which were treated with the samples selected due to their high NO and IL-6 suppressing effect at different concentrations. TNF-alpha included in the supernatant was measured by enzyme-linked immunosorbent assay (TNF-alpha ELISA kit, R&D Systems, MN, USA).

Particularly, 100-fold diluted supernatant was distributed in a 96-well plate on which TNF-alpha antibody was attached, followed by adhesion for 2 hours. The supernatant remaining after the adhesion was washed with a washing buffer. The detection antibody and HRP were adhered on the washed plate for 1 hour. The remaining antibody was washed. Color development was induced by using TMB substrate. The reaction was terminated with sulfuric acid solution. Then, $OD_{450}$ was measured. TNF-alpha in the supernatant was quantified by using the standard curve made with the standard TNF-alpha included in the kit. TNF-alpha suppression rate was calculated by measuring the same concentration that could inhibit TNF-alpha generation up to 50% in the LPS treated group and the results are shown in Table 9.

TABLE 9

| Example | Grades of $IC_{50}$ on TNF-alpha generation (μM) |
|---|---|
| 1 | C |
| 2 | B |
| 4 | A |
| 6 | E |
| 22 | B |
| 24 | C |
| 25 | A |
| 26 | A |
| 28 | A |

(As shown in Table 9, $IC_{50}$ (μM) on TNF-alpha generation according to the compounds of Examples was measured and sorted by the following grades:

A: 1<A≤3;
B: 3<B≤5;
C: 5<C≤10;
D: 10<D≤15; and
E: 15<E≤17.)

As shown in Table 9, the 2-phenylbenzofuran derivatives of the present invention can inhibit TNF-alpha generation at a low concentration, indicating that the derivatives are excellent in suppressing TNF-alpha generation, so that they can be effectively used as a pharmaceutical composition for preventing or treating inflammatory disease.

EXPERIMENTAL EXAMPLE 3

Therapeutic Effect of 2-phenylbenzofuran Derivative on Asthma

To investigate the therapeutic effect of the 2-phenylbenzofuran derivative of the present invention on asthma, the following experiment was performed and the results are shown in Table 9 and FIGS. 1~7.

3-1 Construction of Bronchial Asthma Induced Animal Model and Treatment of Compound 6 week old Balb/c female mice in the average weight of 20 g were adapted for 1 week. 2 mg of aluminum hydroxide (A8222, Sigma, St. Louis, Mo.) and 20 μg of ovalbumin (A5503, sigma, St. Louis, Mo.) were suspended in phosphate buffer (pH 7.4). Each mouse was administered with 200 μl of the phosphate buffer suspension via intraperitoneal injection for sensitization at 2 weeks intervals. The mouse was forced to inhale 1% ovalbumin (OVA) through ultrasonic atomizer for 30 minutes a day for 3 days after the first intraperitoneal injection of ovalbumin. 24 hours after the antigen administration, airway hyperreactivity was measured. 48 hours later, a lethal dose of pentobarbital (Entobar, Hanlim Pharma. Co., Ltd.) was administered to the mouse. The bronchus was opened and the alveoli were washed with 1.4 ml of saline. Then, the test samples were obtained. The normal control (NC) was not administered with ovalbumin nor inhaled. The asthma induced group (OVA) was administered with ovalbumin and inhaled to induce bronchial asthma. The comparative control was orally administered with dexamethasone (2 mg/kg, PO) one hour before the inhalation (DEX). The experimental group was orally administered with the compound of Example 4 of the invention (5 or 15 mg/kg, PO). Each group was composed of 7 Balb/c mice.

3-2. Airway Hyperreactivity Induced by Asthma

After performing the experiment of Experimental Example <3-1> above, airway resistance was measured by using one chamber plethysmography (All Medicus, Seoul) to obtain Penh (enhanced pause) values which were the mathematically calculated numbers reflecting airway obstruction in order to measure airway hyperreactivity. To measure Penh value, basal value in normal breathing status was first measured. Then, the mouse was allowed to intake PBS by using ultrasonic atomizer for 3 minutes. The measurement continued for 3 minutes. Methacholine (A2251, Sigma, St. Louis, Mo.), the histamine used for the general diagnosis of bronchial asthma was treated to the mouse with increasing the concentration from 5 mg/ml and then 10 mg/ml and to 20 mg/ml, followed by measuring Penh values. The results are shown in FIG. 1.

FIG. 1 is a graph illustrating the changes of airway hyperreactivity resulted from asthma development, investigated in Experimental Example <3-2> of the present invention.

As shown in FIG. 1, in the group treated with the compound of Example 4 of the present invention, the increased Penh value resulted from the treatment of OVA was significantly reduced.

3-3. Investigation of Cytokine Production in Bronchoalveolar Lavage Fluid

After performing the experiment of Experimental Example <3-1> above, Th2 cytokine (interleukin 5, 13) in bronchoalveolar was measured by sandwich type enzyme immunoassay. Bronchoalveolar lavage fluid obtained from each experimental group was distributed in a 96-well plate containing cytokine antibody, followed by antigen-antibody reaction at room temperature for 2 hours. To measure the content of interleukin 5 and 13, cytokine specific ELISA kit (R&D System; Minneapolis, Minn.) was used. The content of each cytokine was measured using the kit according to the manufacturer's instruction. The results are shown in FIGS. 2 and 3.

Figure 2:
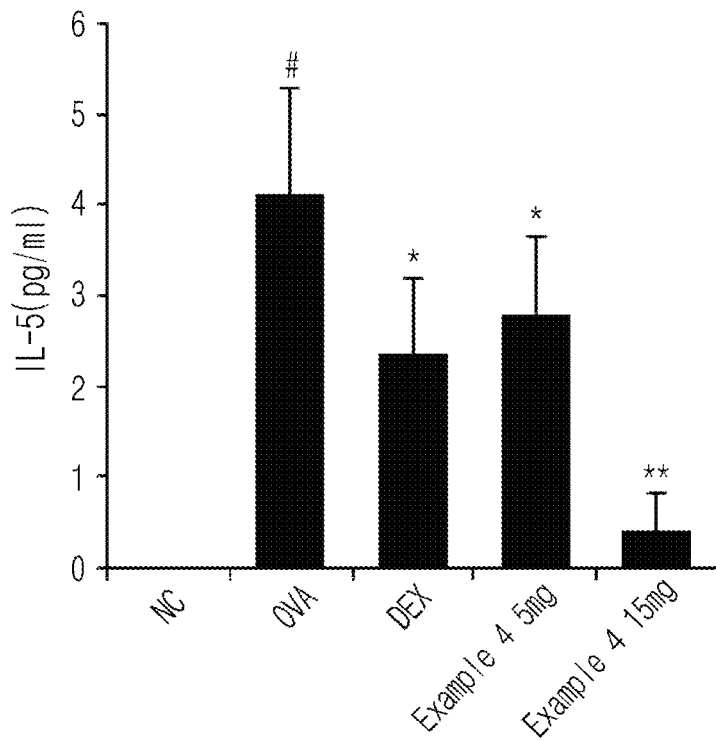
FIG. 2 is a graph illustrating the content of interleukin 5, measured in Experimental Example <3-3> of the present invention.

FIG. 2 is a graph illustrating the content of interleukin 5, measured in Experimental Example <3-3> of the present invention.

Figure 3:
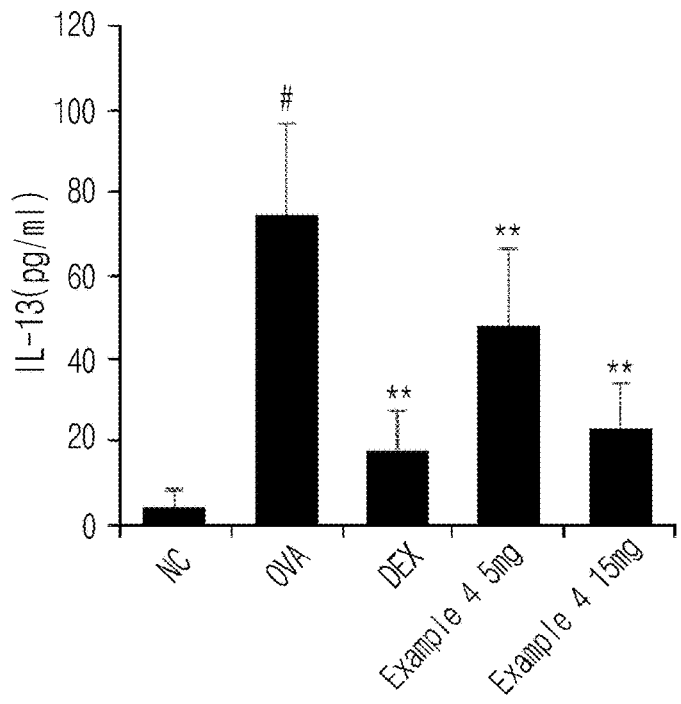
FIG. 3 is a graph illustrating the content of interleukin 13, measured in Experimental Example <3-3> of the present invention.

FIG. 3 is a graph illustrating the content of interleukin 13, measured in Experimental Example <3-3> of the present invention.

As shown in FIG. 2 and FIG. 3, in the group treated with the compound of Example 4 of the invention, the content of interleukin 5 and 13 in bronchoalveolar lavage fluid was significantly reduced.

3-4. Level of Serum IgE

After performing the experiment of Experimental Example <3-1> above, the level of serum IgE relating to the severity of asthma was measured by enzyme immunoassay. A 96-well plate (ELISA plate) was coated with 20 ug/ml of ovalbumin (OVA) dissolved in 0.1 M $NaHCO_3$ buffer (pH 8.3) for overnight at 4° C. Serum taken from each group was distributed in the 96-well plate coated with ovalbumin. Non-specific reaction was blocked by PBS containing 1% bovine serum albumin. The serum sample was diluted at the ratio of 1:400, followed by reaction at room temperature for 2 hours. After washing well, the anti-mouse IgE monoclonal antibody was diluted at the ratio of 1:300, followed by reaction for hours. The plate was reacted with the HRP-conjugated goat anti-rat IgG polyclonal A (1:4000) at room temperature for 1 hour, followed by washing. Color development was induced with 3,3',5,5'-tetramethylbezidine. Then, $OD_{650}$ was measured. The results are shown in FIG. 4.

Figure 4:
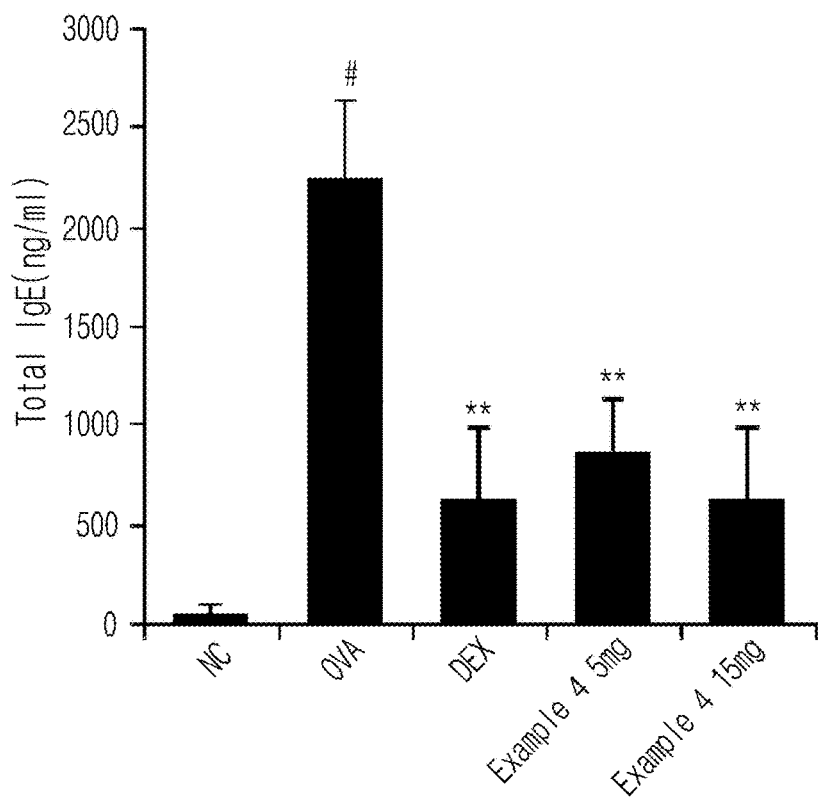
FIG. 4 is a graph illustrating the level of serum IgE, measured in Experimental Example <3-4> of the present invention.

FIG. 4 is a graph illustrating the level of serum IgE, measured in Experimental Example <3-4> of the present invention.

As shown in FIG. 4, the generation of serum IgE induced by OVA was efficiently reduced by the compound of Example 4 of the present invention.

3-5. Number of Inflammatory Cells in Bronchoalveolar Lavage Fluid

After performing the experiment of Experimental Example <3-1> above, the number of inflammatory cells in bronchoalveolar lavage fluid was measured by Diff-Quick staining. The results are shown in FIG. 5.

Figure 5:
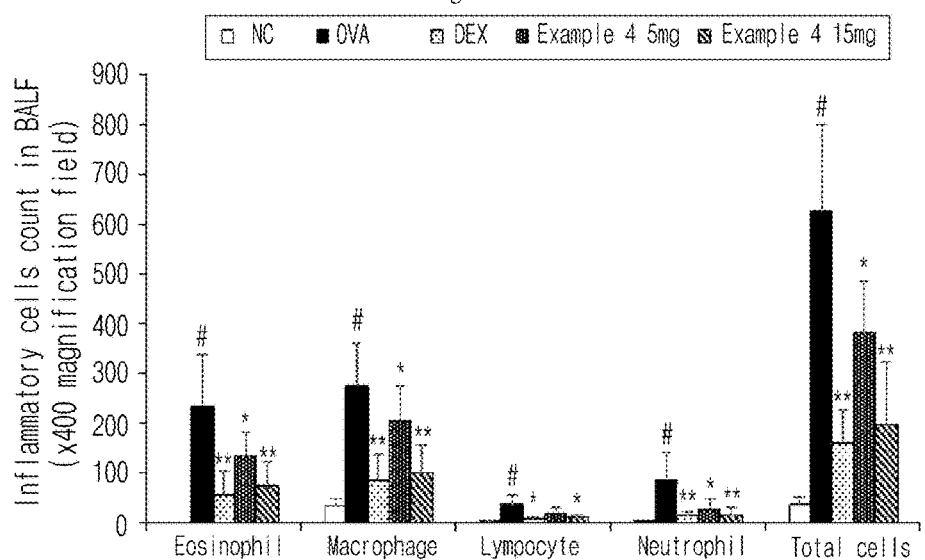
FIG. 5 is a graph illustrating the number of inflammatory cells in bronchoalveolar lavage fluid, measured in Experimental Example <3-5> of the present invention.

FIG. 5 is a graph illustrating the number of inflammatory cells in bronchoalveolar lavage fluid, measured in Experimental Example <3-5> of the present invention.

As shown in FIG. 5, the compound of Example 4 of the present invention could efficiently reduce the infiltration of inflammatory cells (eosinophils) in bronchoalveolar lavage fluid of the mouse induced by OVA.

3-6. Histopathological Analysis

After performing the experiment of Experimental Example <3-1> above, the lung was extracted from the mouse without bronchoalveolar lavage. After formalin fixation and paraffin embedding, 4 μm thick permanent tissue sections were prepared, followed by hematoxylin & eosin (H&E) staining. The results are shown in FIG. 6.

To evaluate the level of mucus production by investigating the increase of the number of goblet cells, the mucus secretion cells, the lung was extracted from the mouse without bronchoalveolar lavage. After formalin fixation and paraffin embedding, 4 μm thick permanent tissue sections were prepared, followed by Periodic acid Schiff (PAS) staining. The proliferation of goblet cells was evaluated by measuring the ratio of the goblet cells selected by the staining above in bronchial epithelial cells. The results are shown in FIG. 7.

Figure 6:
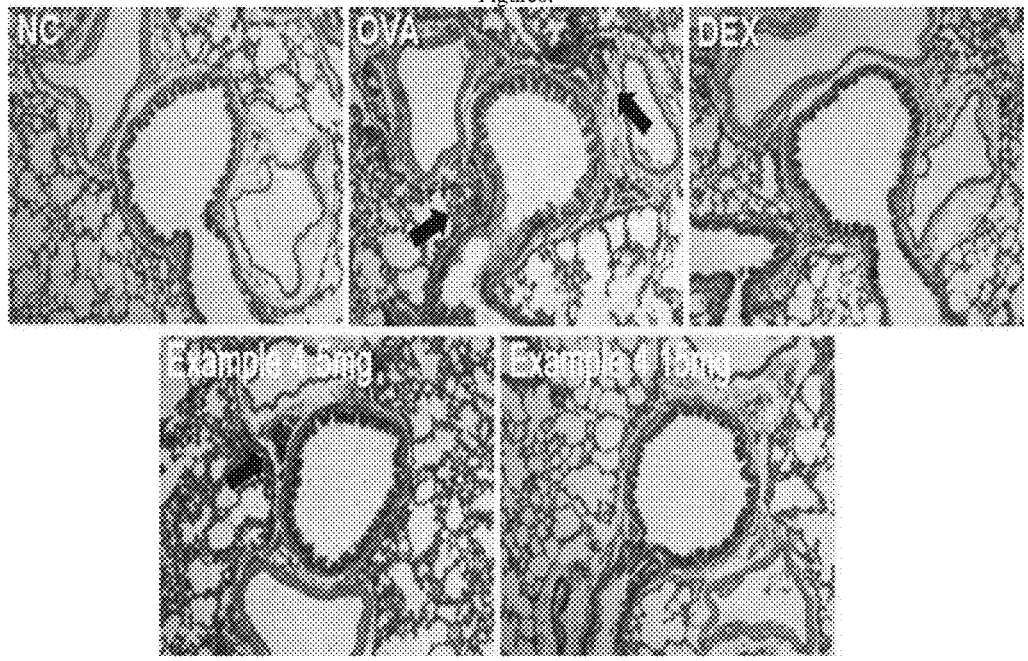
FIG. 6 is an image illustrating the lung tissue sections of the asthma induced mouse, wherein the sections were stained with hematoxylin & eosin (H&E) in Experimental Example <3-6> of the present invention.

FIG. 6 is an image illustrating the lung tissue sections of the asthma induced mouse, wherein the sections were stained with hematoxylin & eosin (H&E) in Experimental Example <3-6> of the present invention.

Figure 7:
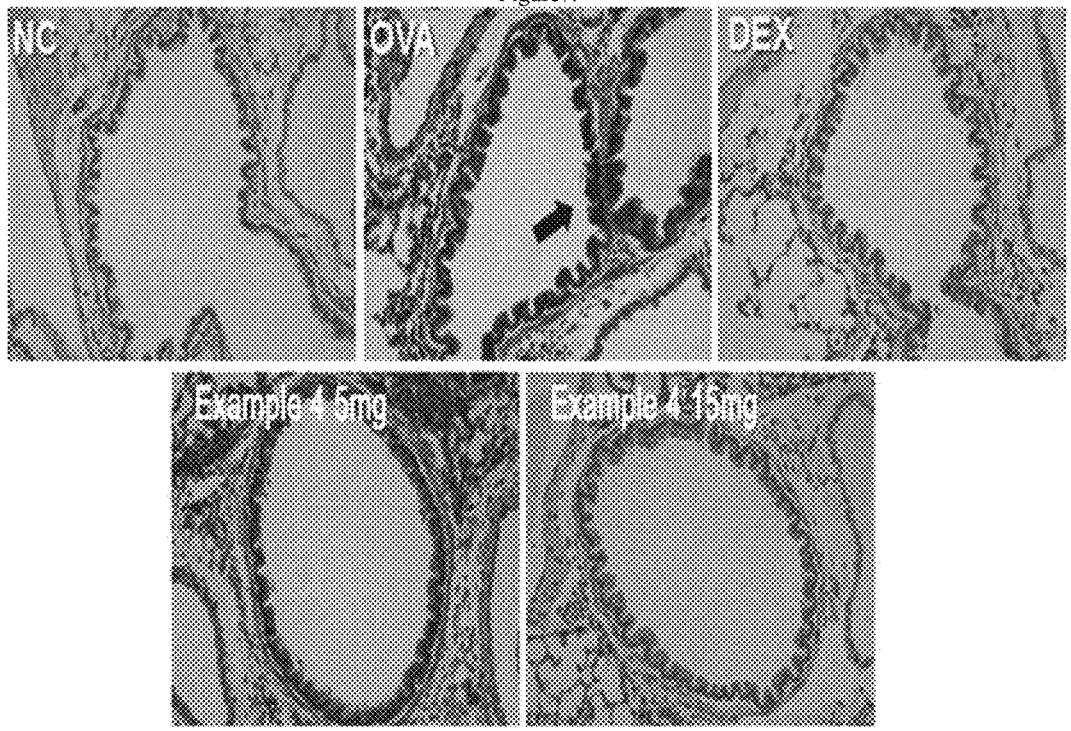
FIG. 7 is an image illustrating the lung tissue sections of the asthma induced mouse, wherein the sections were stained with Periodic acid Schiff (PAS) in Experimental Example <3-6> of the present invention.

FIG. 7 is an image illustrating the lung tissue sections of the asthma induced mouse, wherein the sections were stained with Periodic acid Schiff (PAS) in Experimental Example <3-6> of the present invention.

As shown in FIG. 6, numbers of inflammatory cells including eosinophils were accumulated in around bronchiole in the asthma induced group (OVA), while the accumulation of inflammatory cells in the group treated with the compound of Example 4 of the invention was significantly reduced.

As shown in FIG. 7, the proliferation of goblet cells was significantly reduced in the group treated with the compound of Example 4 of the invention, confirmed by the reduction of the mucus production.

From the results of Experimental Example 3, it was confirmed that the 2-phenylbenzofuran derivative of the present invention had the therapeutic effect on asthma.

EXPERIMENTAL EXAMPLE 4

Toxicity Test of 2-phenylbenzofuran Derivative

Toxicity test was performed as follows to confirm the toxicity of the 2-phenylbenzofuran derivative of the present invention. The results are shown in Tables 10~14 and FIGS. 8~9.

1. Test Material and Control Material
Test material: compound of Example 4
Storage condition: frozen storage
Control material: 10% DMSO+10% Tween 20 in PBS
2. Test System
Animal: female Balb/c
Animal provider: Koatech
Age and weight of animal
    Age at the time of arrival: 5 week
    Number at the time of arrival: 28
    Age at the start of administration: 6 week
    Number at the start of administration: 28÷
    Weight at the start of administration: 16.1~16.5 g
3. Administration Method and Preparation of Test Material
Administration method: single oral administration
Preparation of test material: Test materials were prepared by using 10% DMSO+10% Tween-20 in PBS as a solvent for each dose. The preparation was carried out immediately before the administration
4. Observation Item and Test Item
General Symptoms and Observation of Dead Animals
General symptoms, toxic symptoms and presence of dead animals were observed every hour from one to five hours after the last administration on the day of administration and once a day from the next day to the $9^{th}$ day from the final administration.

Measurement of Weight
All the animals used in the test were weighed on days 1, 7, 8, 9 and 10 before the administration
Autopsy Findings
On the $10^{th}$ day after the administration, all the surviving animals were anesthetized with $CO_2$ gas. Laparotomy was performed and the animals were sacrificed by venesection from the abdominal aorta. Then, all the internal organs of the animal were observed by the naked eye.

5. Results of Toxicity Test of the Compound of Example 4

The compound of Example 4 was orally administered once to female Balb/c mouse at the doses of 250, 500, and 1000 mg/kg in order to obtain the information on acute toxicity of the compound of Example 4, followed by investigation of death rate, general symptoms, and weight changes for 10 days by autopsy. The results are shown in Tables 10~14 and FIGS. 8~9.

1) Weight Change

Figure 8:
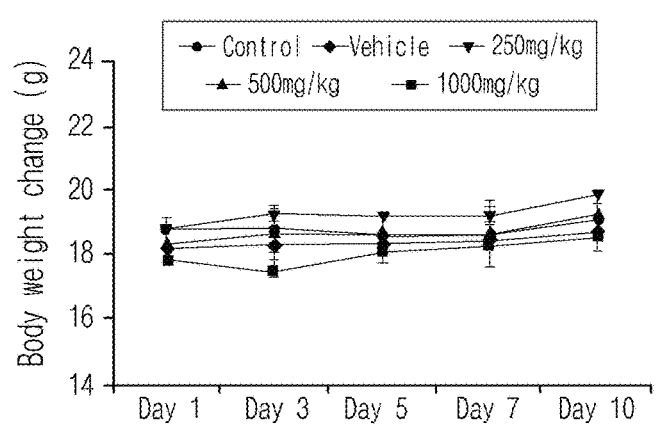
FIG. 8 is a graph illustrating the weight changes of the mouse used in toxicity test performed in Experimental Example 4 of the present invention.

Weight changes were measured and the results are shown in FIG. 8 and Table 10.

FIG. 8 is a graph illustrating the weight changes of the mouse used in toxicity test performed in Experimental Example 4 of the present invention.

Table 10 shows the weight changes of the mouse used in toxicity test performed in Experimental Example 4 of the present invention.

TABLE 10

| Group | | Day 1 | Day 3 | Day 5 | Day 7 | Day 10 |
|---|---|---|---|---|---|---|
| Control | | 18.74 ± 0.4 | 18.82 ± 0.5 | 18.72 ± 0.4 | 18.58 ± 0.4 | 19.08 ± 0.5 |
| Vehicle | | 18.14 ± 0.2 | 18.28 ± 0.3 | 18.28 ± 0.2 | 18.38 ± 0.2 | 18.78 ± 0.4 |
| Example 4 (mg/kg) | 250 | 18.73 ± 0.8 | 19.21 ± 0.7 | 19.17 ± 0.9 | 19.19 ± 1.1 | 19.77 ± 1.1 |
| | 500 | 18.21 ± 0.7 | 18.54 ± 1.0 | 18.54 ± 0.7 | 18.66 ± 0.9 | 19.11 ± 0.8 |
| | 1000 | 17.77 ± 0.5 | 17.41 ± 0.6 | 18.01 ± 0.4 | 18.26 ± 0.7 | 18.51 ± 0.5 |

As shown in FIG. 8 and Table 10, the weight changes of the mice administered with the compound of Example 4 of the invention were not observed by the end of the test (Day 10).

2) General Symptoms

The general symptom evaluation results are shown in Table 11 below.

Table 11 shows the general symptom evaluation results of the mouse used in toxicity test performed in Experimental Example 4 of the present invention.

As shown in Table 11, hair loss, abnormal walking, depression and diarrhea due to administration of the compound of Example 4 were not observed.

3) Toxicological Changes in Organs

After the administration of the compound of Example 4, the mice were autopsied on the last day, and the toxicological changes in the abdomen, chest and major organs were observed. The results are shown in Table 12 and FIG. 9.

Figure 9:
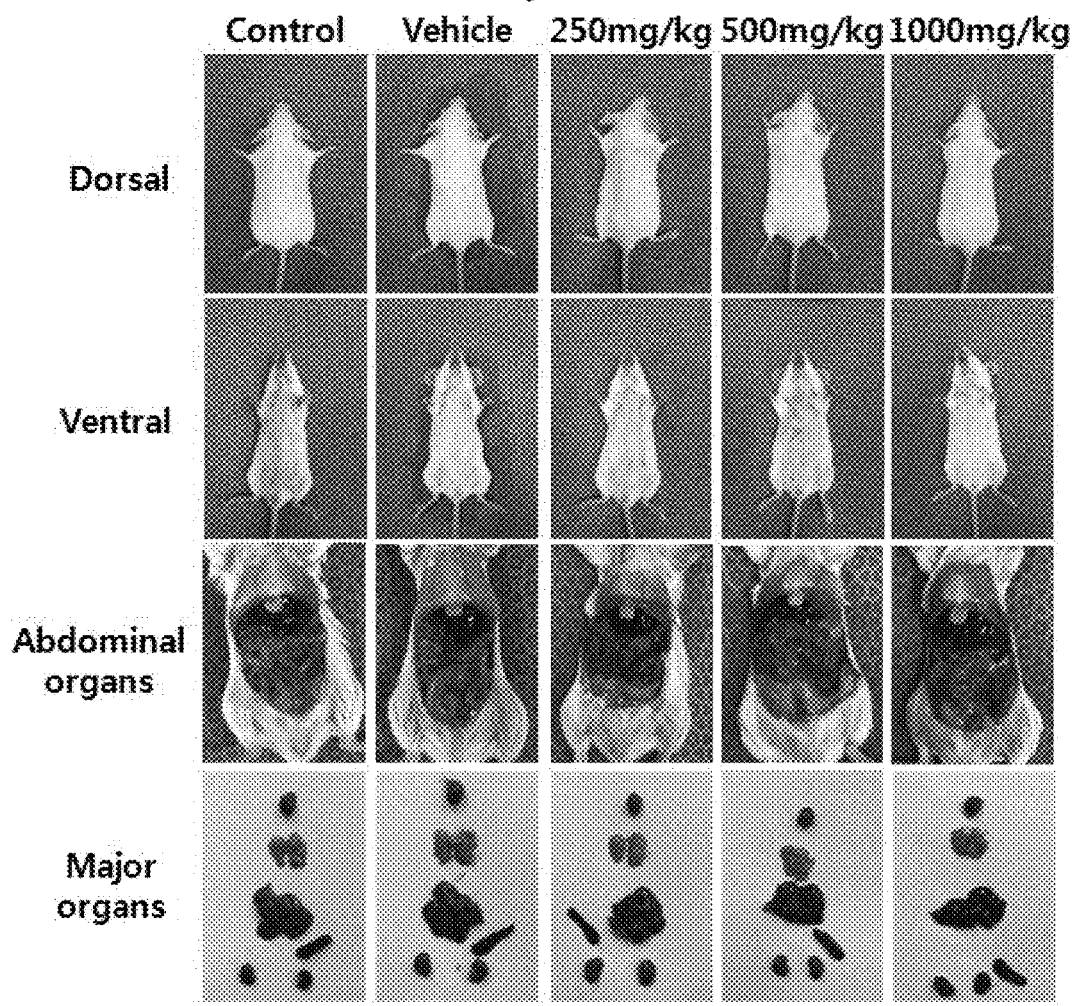
FIG. 9 is an image illustrating the abdomen, chest and major organs of the mouse used in toxicity test performed in Experimental Example 4 of the present invention.

FIG. 9 is an image illustrating the abdomen, chest and major organs of the mouse used in toxicity test performed in Experimental Example 4 of the present invention.

Table 12 shows the toxicological changes in the abdomen, chest and major organs of the mouse used in toxicity test performed in Experimental Example 4 of the present invention.

TABLE 11

| Group | | Clinical sign | Day 1 | Day 3 | Day 5 | Day 7 | Day 10 | Total |
|---|---|---|---|---|---|---|---|---|
| Control | | Loss of fur | 0/5 | 0/5 | 0/5 | 0/5 | 0/5 | 0 |
| | | Abnormal gait | 0/5 | 0/5 | 0/5 | 0/5 | 0/5 | 0 |
| | | Depression | 0/5 | 0/5 | 0/5 | 0/5 | 0/5 | 0 |
| | | Diarrhea | 0/5 | 0/5 | 0/5 | 0/5 | 0/5 | 0 |
| Vehicle | | Loss of fur | 0/5 | 0/5 | 0/5 | 0/5 | 0/5 | 0 |
| | | Abnormal gait | 0/5 | 0/5 | 0/5 | 0/5 | 0/5 | 0 |
| | | Depression | 0/5 | 0/5 | 0/5 | 0/5 | 0/5 | 0 |
| | | Diarrhea | 0/5 | 0/5 | 0/5 | 0/5 | 0/5 | 0 |
| Example 4 (mg/kg) | 250 | Loss of fur | 0/7 | 0/7 | 0/7 | 0/7 | 0/7 | 0 |
| | | Abnormal gait | 0/7 | 0/7 | 0/7 | 0/7 | 0/7 | 0 |
| | | Depression | 0/7 | 0/7 | 0/7 | 0/7 | 0/7 | 0 |
| | | Diarrhea | 0/7 | 0/7 | 0/7 | 0/7 | 0/7 | 0 |
| | 500 | Loss of fur | 0/7 | 0/7 | 0/7 | 0/7 | 0/7 | 0 |
| | | Abnormal gait | 0/7 | 0/7 | 0/7 | 0/7 | 0/7 | 0 |
| | | Depression | 0/7 | 0/7 | 0/7 | 0/7 | 0/7 | 0 |
| | | Diarrhea | 0/7 | 0/7 | 0/7 | 0/7 | 0/7 | 0 |
| | 1000 | Loss of fur | 0/7 | 0/7 | 0/7 | 0/7 | 0/7 | 0 |
| | | Abnormal gait | 0/7 | 0/7 | 0/7 | 0/7 | 0/7 | 0 |
| | | Depression | 0/7 | 0/7 | 0/7 | 0/7 | 0/7 | 0 |
| | | Diarrhea | 0/7 | 0/7 | 0/7 | 0/7 | 0/7 | 0 |

TABLE 12

| Group | | Clinical sign | Day 1 | Day 7 | Day 8 | Day 9 | Day 10 | Total |
|---|---|---|---|---|---|---|---|---|
| Control | | Abdominal cavity | 0/5 | 0/5 | 0/5 | 0/5 | 0/5 | 0 |
| | | Thoracic cavity | 0/5 | 0/5 | 0/5 | 0/5 | 0/5 | 0 |
| | | Major organs | 0/5 | 0/5 | 0/5 | 0/5 | 0/5 | 0 |
| | | Mortality | 0/5 | 0/5 | 0/5 | 0/5 | 0/5 | 0 |
| Vehicle | | Abdominal cavity | 0/5 | 0/5 | 0/5 | 0/5 | 0/5 | 0 |
| | | Thoracic cavity | 0/5 | 0/5 | 0/5 | 0/5 | 0/5 | 0 |
| | | Major organs | 0/5 | 0/5 | 0/5 | 0/5 | 0/5 | 0 |
| | | Mortality | 0/5 | 0/5 | 0/5 | 0/5 | 0/5 | 0 |
| Example 4 (mg/kg) | 250 | Abdominal cavity | 0/7 | 0/7 | 0/7 | 0/7 | 0/7 | 0 |
| | | Thoracic cavity | 0/7 | 0/7 | 0/7 | 0/7 | 0/7 | 0 |
| | | Major organs | 0/7 | 0/7 | 0/7 | 0/7 | 0/7 | 0 |
| | | Mortality | 0/7 | 0/7 | 0/7 | 0/7 | 0/7 | 0 |
| | 500 | Abdominal cavity | 0/7 | 0/7 | 0/7 | 0/7 | 0/7 | 0 |
| | | Thoracic cavity | 0/7 | 0/7 | 0/7 | 0/7 | 0/7 | 0 |
| | | Major organs | 0/7 | 0/7 | 0/7 | 0/7 | 0/7 | 0 |
| | | Mortality | 0/7 | 0/7 | 0/7 | 0/7 | 0/7 | 0 |
| | 1000 | Abdominal cavity | 0/7 | 0/7 | 0/7 | 0/7 | 0/7 | 0 |
| | | Thoracic cavity | 0/7 | 0/7 | 0/7 | 0/7 | 0/7 | 0 |
| | | Major organs | 0/7 | 0/7 | 0/7 | 0/7 | 0/7 | 0 |
| | | Mortality | 0/7 | 0/7 | 0/7 | 0/7 | 0/7 | 0 |

As shown in FIG. 9 and Table 12, the toxicological changes (changes in the abdomen, chest and major organs) due to administration of the compound of Example 4 were not observed.

5) Weight Changes of Organs

After administration of the compound, mice were autopsied on the last day, and the weight of the major organs was measured absolutely and relatively. The results are shown in Tables 13 and 14.

Table 13 shows the absolute weight of the major organs of the mouse used in toxicity test performed in Experimental Example 4 of the present invention.

TABLE 13

| Group | | Heart | | Lung | | Liver | | Spleen | | Kidney Left | | Kidney Right | |
|---|---|---|---|---|---|---|---|---|---|---|---|---|---|
| Control | | 0.09 ± 0.004 | | 0.13 ± 0.017 | | 0.91 ± 0.077 | | 0.07 ± 0.007 | | 0.12 ± 0.013 | | 0.12 ± 0.012 | |
| Vehicle | | 0.10 ± 0.005 | p value | 0.13 ± 0.009 | p value | 0.80 ± 0.013 | p value | 0.07 ± 0.011 | p value | 0.12 ± 0.002 | p value | 0.12 ± 0.005 | p value |
| Example 4 (mg/kg) | 250 | 0.09 ± 0.008 | 0.390 | 0.12 ± 0.005 | 0.006 | 0.81 ± 0.054 | 0.042 | 0.07 ± 0.015 | 0.061 | 0.12 ± 0.013 | 0.090 | 0.11 ± 0.011 | 0.254 |
| | 500 | 0.09 ± 0.010 | 0.220 | 0.12 ± 0.013 | 0.072 | 0.81 ± 0.071 | 0.057 | 0.07 ± 0.009 | 0.007 | 0.11 ± 0.008 | 0.009 | 0.11 ± 0.005 | 0.046 |
| | 1000 | 0.09 ± 0.005 | 0.004 | 0.12 ± 0.013 | 0.322 | 0.80 ± 0.030 | 0.391 | 0.07 ± 0.012 | 0.226 | 0.11 ± 0.007 | 0.002 | 0.11 ± 0.005 | 0.300 |

Table 14 shows the relative weight of the major organs of the mouse used in toxicity test performed in Experimental Example 4 of the present invention.

TABLE 14

| Group | | Heart | | Lung | | Liver | | Spleen | | Kidney Left | | Kidney Right | |
|---|---|---|---|---|---|---|---|---|---|---|---|---|---|
| Control | | 0.48 ± 0.019 | | 0.68 ± 0.091 | | 4.74 ± 0.322 | | 0.38 ± 0.059 | | 0.64 ± 0.057 | | 0.63 ± 0.052 | |
| Vehicle | | 0.51 ± 0.035 | p value | 0.67 ± 0.045 | p value | 4.24 ± 0.109 | p value | 0.39 ± 0.057 | p value | 0.64 ± 0.018 | p value | 0.62 ± 0.037 | p value |
| Example 4 (mg/kg) | 250 | 0.47 ± 0.046 | 0.089 | 0.63 ± 0.022 | 0.001 | 4.10 ± 0.238 | 0.005 | 0.36 ± 0.069 | 0.013 | 0.59 ± 0.059 | 0.007 | 0.58 ± 0.057 | 0.046 |
| | 500 | 0.47 ± 0.041 | 0.069 | 0.65 ± 0.066 | 0.044 | 4.21 ± 0.283 | 0.019 | 0.36 ± 0.040 | 0.001 | 0.58 ± 0.039 | 0.001 | 0.59 ± 0.027 | 0.020 |
| | 1000 | 0.46 ± 0.038 | 0.024 | 0.66 ± 0.065 | 0.416 | 4.32 ± 0.196 | 0.203 | 0.37 ± 0.074 | 0.295 | 0.59 ± 0.041 | 0.013 | 0.61 ± 0.021 | 0.310 |

As shown in Tables 13 and 14, the absolute/relative weight changes of the major organs (heart, lung, liver, spleen, and kidney) due to administration of the compound of Example 4 were not observed.

From the results of Experimental Example 4, it was confirmed that the 2-phenylbenzofuran derivative of the present invention had no toxicity.

EXPERIMENTAL EXAMPLE 5

Therapeutic Effect of 2-phenylbenzofuran on Rheumatoid Arthritis

To investigate the therapeutic effect of the 2-phenylbenzofuran derivative of the present invention on rheumatoid arthritis, the following experiment was performed and the results are shown in FIGS. 10~13.

1. Preparation of Rheumatoid Arthritis Animal Model

Bovine type II collagen (100 µg/mouse, Hondrax, Seattle, USA) and complete Freund's adjuvant (Chondrex, Seattle, USA) were intradermally injected in the tail of 7~9 DBA/1 male mouse. On day 21, 100 µg of bovine type II collagen was mixed with incomplete Freund's adjuvant (IFA), which was injected in the tail of each mouse once again to induce arthritis.

2. Solvent Composition

The compound of Example 25 of the invention was dissolved in a solvent (10% DMAC+10% Tween 80 in PBS).

3. Administration Pathway and Treatment Group

Administration pathway: Oral administration Group (6 per group)

Vehicle control group (CIA group)
Dexamethasone (0.3 mg/kg)—positive control group
Example 25 compound group (30 mg/kg)

4. Therapeutic Effect on Rheumatoid Arthritis

1) Measurement of Weight Changes

Figure 10:
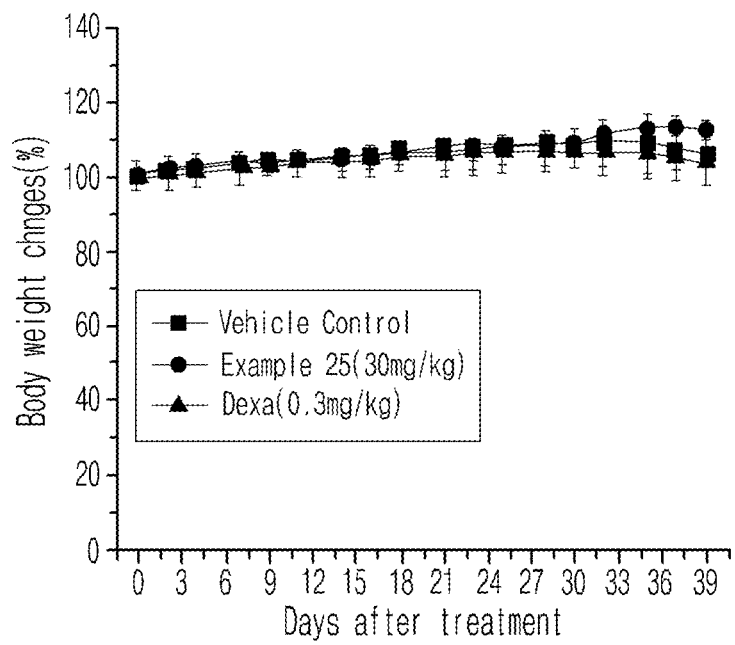
FIG. 10 is a graph illustrating the weight changes of each experimental group mouse, measured in Experimental Example 5 of the present invention.

Weight changes were measured and the results are shown in FIG. 10.

FIG. 10 is a graph illustrating the weight changes of each experimental group mouse, measured in Experimental Example 5 of the present invention.

As shown in FIG. 10, there was no weight change observed in the mouse treated with the compound of Example 25 of the present invention.

2) Measurement of Paw Edema (Clinical Score)

The most representative symptom, edema, of arthritis is caused when macrophages, T lymphocytes, and B lymphocytes move to the joint synovial membrane tissue to accelerate inflammatory response accompanying pain. Thus, the inhibitory effect of the compound of Example 25 of the present invention on edema was investigated. To evaluate the inhibitory effect on edema, the condition of edema was observed once a week for the first 21 days and then twice a week from day 21 by the naked eye. At least two participants were involved in the observation and the results were statistically calculated. The results are shown in FIG. 11 and FIG. 12.

Figure 11:
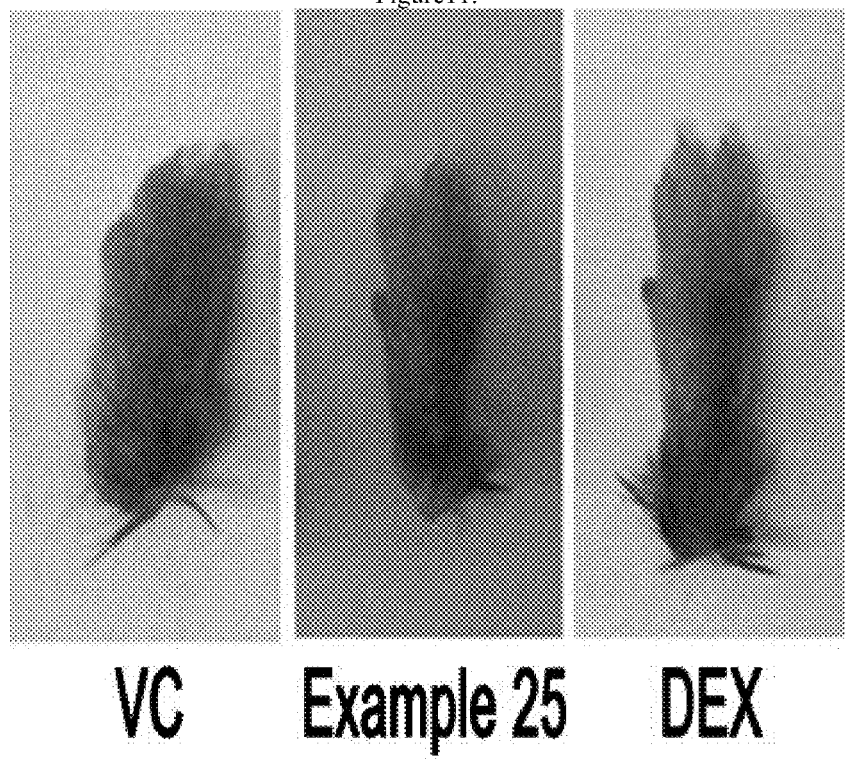
FIG. 11 is an image illustrating the foot of each experimental group mouse, photographed in Experimental Example 5 of the present invention.

0; no edema or swelling observed
1; light edema and redness observed in limited areas of ankle joint and tarsal bone
2; light edema and redness observed in the area covering from ankle joint to tarsal bone
3; severe edema and redness observed in the area covering from ankle joint to tarsal bone
4; edema and redness observed all over the area of ankle and the entire toes FIG. 11 is an image illustrating the foot of each experimental group mouse, photographed in Experimental Example 5 of the present invention.

Figure 12:
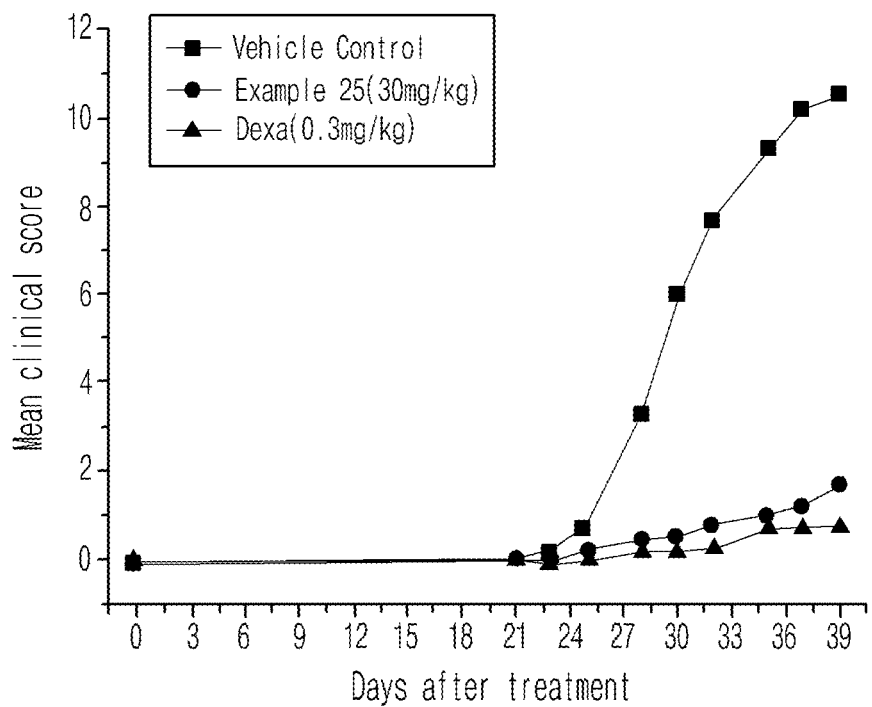
FIG. 12 is a graph illustrating the results of paw edema evaluation (clinical score) obtained from the observation of each experimental group mouse in Experimental Example 5 of the present invention.

FIG. 12 is a graph illustrating the results of paw edema evaluation (clinical score) obtained from the observation of each experimental group mouse in Experimental Example 5 of the present invention.

As shown in FIGS. 11 and 12, the treatment of the compound of Example 15 of the invention suppressed edema in the foot induced by collagen up to the level of the positive control treated with dexamethasone.

3) Inhibitory Effect on the Production of Inflammatory Cytokine According to the Treatment of the Compound ELISA was performed with the serum and foot to investigate whether or not the compound of the invention could suppress the generation of TNF-alpha and interleukin-6, the inflammatory cytokines known as the promoter of inflammation which is the common symptom of acute and chronic arthritis. The results are shown in FIG. 13 and FIG. 14.

Figure 13:
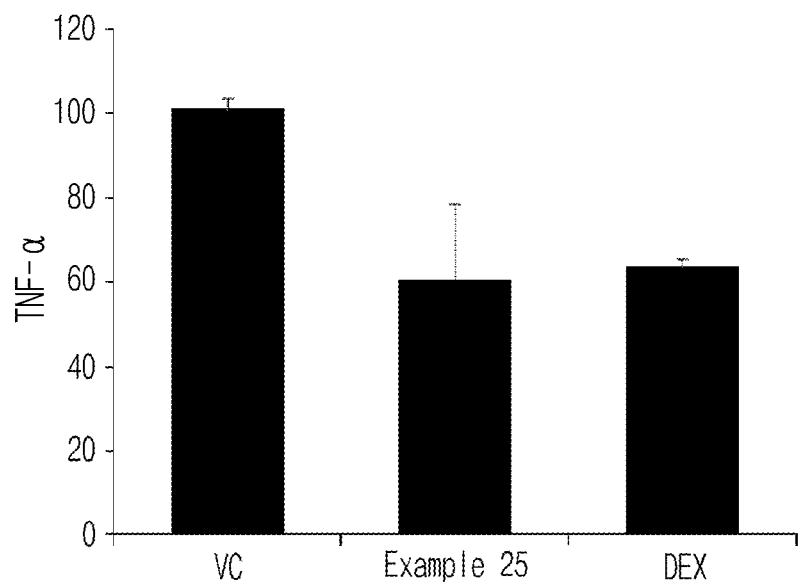
FIG. 13 is a graph illustrating the production of TNF-alpha measured in Experimental Example 5 of the present invention.

FIG. 13 is a graph illustrating the production of TNF-alpha measured in Experimental Example 5 of the present invention.

Figure 14:
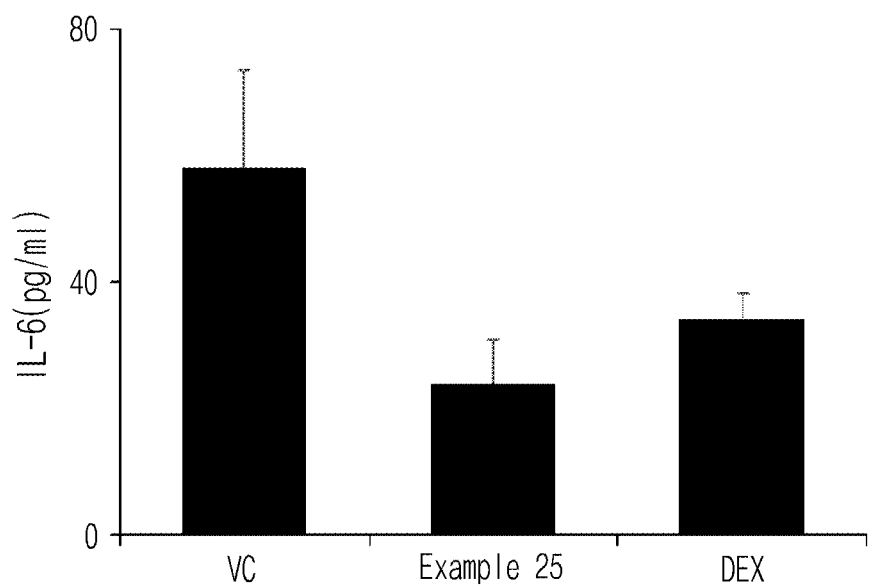
FIG. 14 is a graph illustrating the production of interleukin-6 measured in Experimental Example 5 of the present invention.

FIG. 14 is a graph illustrating the production of interleukin-6 measured in Experimental Example 5 of the present invention.

As shown in FIG. 13 and FIG. 14, when the compound of Example 15 of the invention was treated, the generation of inflammatory cytokines TNF-alpha and interleukin-6 induced by collagen was inhibited.

From the results of Experimental Example 5, it was confirmed that the 2-phenylbenzofuran derivative of the present invention had the therapeutic effect on rheumatoid arthritis.

MANUFACTURING EXAMPLE 1

Preparation of Pharmaceutical Formulations

<1-1> Preparation of Powders

The derivative represented by formula 1 or formula 2 2 g

| Lactose | 1 g |
|---------|-----|

Powders were prepared by mixing all the above components, which were filled in airtight packs according to the conventional method for preparing powders.

<1-2> Preparation of Tablets

The derivative represented by formula 1 or formula 2 100 mg

| Corn starch | 100 mg |
|---|---|
| Lactose | 100 mg |
| Magnesium stearate | 2 mg |

Tablets were prepared by mixing all the above components by the conventional method for preparing tablets.

<1-3> Preparation of Capsules

The derivative represented by formula 1 or formula 2 100 mg

| Corn starch | 100 mg |
|---|---|
| Lactose | 100 mg |
| Magnesium stearate | 2 mg |

Capsules were prepared by mixing all the above components, which were filled in gelatin capsules according to the conventional method for preparing capsules.

<1-4> Preparation of Injectable Solutions

The derivative represented by formula 1 or formula 2 10 μg/ml

| | |
|---|---|
| Weak HCl BP | until pH 3.5 |
| Injectable NaCl BP | up to 1 ml |

The compound of the invention was dissolved in proper volume of injectable NaCl BP. pH of the prepared solution was regulated as 3.5 by using weak HCl BP. The volume was adjusted by using injectable NaCl BP. The solution was well mixed and filled in 5 ml type I transparent glass ampoules. The ampoules were sealed by melting the glass of opening, followed by autoclave at 120° C. for at least 15 minutes for sterilization.

MANUFACTURING EXAMPLE 2

Preparation of Health Food

The derivative represented by formula 1 or formula 2 500 ng

| | proper amount |
|---|---|
| Vitamin complex | |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Minerals | |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food was prepared according to the conventional method.

MANUFACTURING EXAMPLE 3

Preparation of Health Beverages

The derivative represented by formula 1 or formula 2 500 ng

| | |
|---|---|
| Citric acid | 1000 mg |
| Oligosaccharide | 100 g |
| Maesil (Prunus mume) Extract | 2 g |
| Taurine | 1 g |
| Purified water | up to 900 ml |

The above constituents were mixed according to the conventional method for preparing health beverages. The mixture was heated at 85° C. for 1 hour with stirring and then filtered. The filtrate was loaded in 2 liter steri-CLAIMSlized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A compound selected from the group consisting of:
   3-(7-methoxy-2-p-tolylbenzofuran-5-yl)propane-1-ol; and
   4-(5-(3-hydroxypropyl)-7-methoxybenzofuran-2-yl)benzene-1,2-diol or a pharmaceutically acceptable salt of the same.

2. A method for preparing the compound of claim 1 comprising the following steps, as shown in reaction formula 3:
   preparing the compound represented by formula 8 by reacting the compound represented by formula 5 with the compound represented by formula 7 in the presence of a base catalyst (step 1);
   preparing the compound represented by formula 9 by inducing hydrogenation of the compound represented by formula 8 obtained in step 1 in the presence of an acid using palladium charcoal as a catalyst (step 2); and
   preparing the compound represented by formula 1c by reducing the compound represented by formula 9 obtained in step 2 in the presence of sodium borohydride (step 3):

[Reaction Formula 3]

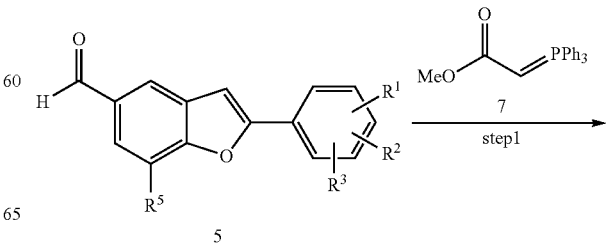

-continued

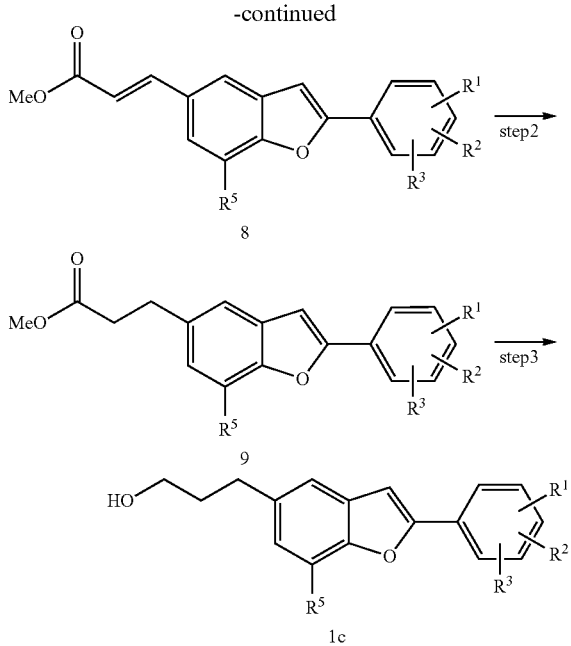

wherein, $R^1$, $R^2$, and $R^3$ are independently selected from the group consisting of hydroxyl and methyl;
$R^5$ is methoxy; and
the compound represented by formula 1c is a derivative of the compound of claim 1.

3. A pharmaceutical composition for treating inflammatory disease comprising the compound of claim 1 or the pharmaceutically acceptable salt thereof as an active ingredient.

4. The pharmaceutical composition for treating inflammatory disease according to claim 3, wherein the inflammatory disease is selected from the group consisting of dermatitis, allergy, atopy, conjunctivitis, periodontitis, rhinitis, otitis media, laryngopharyngitis, tonsilitis, pneumonia, gastric ulcer, gastritis, Crohn's disease, colitis, hemorrhoid, gout, ankylosing spondylitis, rheumatic fever, lupus, fibromyalgia, psoriatic arthritis, osteoarthritis, rheumatoid arthritis, periarthritis of shoulder, tendinitis, tenosynovitis, peritendinitis, dermatitis, hepatitis, cystitis, nephritis, Sjogren's syndrome, multiple sclerosis, asthma, COPD(Chronic Obstructive Pulmonary Disease) and acute or chronic inflammatory disease.

5. The pharmaceutical composition for treating inflammatory disease according to claim 3, wherein the compound according to claim 1 characteristically suppresses the generation of nitric oxide (NO) induced by immune response.

6. The pharmaceutical composition for treating inflammatory disease according to claim 3, wherein the compound according to claim 1 characteristically suppresses the generation of interleukin-6 (IL-6) induced by immune response.

7. The pharmaceutical composition for treating inflammatory disease according to claim 3, wherein the compound according to claim 1 characteristically suppresses the generation of TNF-alpha induced by immune response.

8. A health food composition for improving inflammatory disease comprising the compound according to claim 1 or the pharmaceutically acceptable salt thereof as an active ingredient.

9. A method of treating asthma, the method comprising administering to a subject in need an effective amount of 3-(7-methoxy-2-p-tolylbenzofuran-5-yl)propane-1-ol or the pharmaceutically acceptable salt thereof.

10. A method of treating rheumatoid arthritis, the method comprising administering to a subject in need an effective amount of 4-(5-(3-hydroxypropyl)-7-methoxybenzofuran-2-yl)benzene-1,2-diol or the pharmaceutically acceptable salt thereof.

* * * * *